(12) United States Patent
Ahmed

(10) Patent No.: US 12,239,511 B2
(45) Date of Patent: Mar. 4, 2025

(54) BODY FLUID MANAGEMENT INSERTS AND GARMENTS

(71) Applicant: Wesam Fawz Ahmed, Sydney (AU)

(72) Inventor: Wesam Fawz Ahmed, Sydney (AU)

(73) Assignee: Wesam Fawz Ahmed, Sydney (AU)

( * ) Notice: Subject to any disclaimer, the term of this patent is extended or adjusted under 35 U.S.C. 154(b) by 0 days.

(21) Appl. No.: 18/685,842

(22) PCT Filed: Aug. 25, 2022

(86) PCT No.: PCT/AU2022/051004
§ 371 (c)(1),
(2) Date: Feb. 22, 2024

(87) PCT Pub. No.: WO2023/023777
PCT Pub. Date: Mar. 2, 2023

(65) Prior Publication Data
US 2024/0261155 A1    Aug. 8, 2024

(30) Foreign Application Priority Data
Aug. 25, 2021   (AU) ................ 2021221700

(51) Int. Cl.
*A61F 13/15*    (2006.01)
*A61F 13/505*   (2006.01)
*A61F 13/535*   (2006.01)

(52) U.S. Cl.
CPC ...... *A61F 13/15268* (2013.01); *A61F 13/505* (2013.01); *A61F 13/535* (2013.01); *A61F 2013/5355* (2013.01)

(58) Field of Classification Search
CPC .......... A61F 13/15268; A61F 13/49003; A61F 13/49006; A61F 13/532; A61F 13/535;
(Continued)

(56) References Cited

U.S. PATENT DOCUMENTS 3,838,693 A  * 10/1974  Sherman ........... A61F 13/49003
                                                             604/386
4,315,507 A    2/1982  Whitehead et al.
(Continued)

FOREIGN PATENT DOCUMENTS

EP    0570016 A1    11/1993
EP    3437604       2/2019
(Continued)

OTHER PUBLICATIONS

International Search Report and Written Opinion in related PCT Application PCT/AU2022/051004 mailed Oct. 12, 2022, 29 pages.
(Continued)

*Primary Examiner* — Catharine L Anderson
(74) *Attorney, Agent, or Firm* — HOVEY WILLIAMS LLP

(57) ABSTRACT

An insert for a garment, the insert comprising a liquid barrier layer having a wearer-facing side; and an absorbent layer disposed adjacent to the wearer-facing side of the liquid barrier layer; wherein the absorbent layer covers a portion of the wearer-facing side of the liquid barrier layer but leaves at least a portion of a peripheral region of the wearer-facing side uncovered.

20 Claims, 28 Drawing Sheets

(58) Field of Classification Search
CPC .. A61F 2013/15276; A61F 2013/53445; A61F 2013/5355
See application file for complete search history.

(56) References Cited

U.S. PATENT DOCUMENTS

| | | | |
|---|---|---|---|
| 5,389,094 | A | 2/1995 | Lavash et al. |
| 9,003,571 | B1 | 4/2015 | Lewis-Williams |
| 11,154,431 | B1* | 10/2021 | Yip ........................ A41B 17/00 |
| 11,207,225 | B2* | 12/2021 | Kajanthan ......... A61F 13/49446 |
| 11,752,043 | B2* | 9/2023 | Siriwardene ........... A41B 9/0012/400 |
| 2007/0287977 | A1 | 12/2007 | Fujikawa et al. |
| 2011/0172621 | A1 | 7/2011 | Lee et al. |
| 2016/0184146 | A1* | 6/2016 | Tulk ....................... A01N 37/06 604/385.15 |
| 2018/0014983 | A1* | 1/2018 | Jayasuriya .............. A61L 15/26 |
| 2021/0030605 | A1 | 2/2021 | Kajanthan et al. |
| 2021/0100698 | A1* | 4/2021 | Langdon ........... A61F 13/49006 |
| 2022/0354710 | A1* | 11/2022 | Sepello ............. A61F 13/49446 |

FOREIGN PATENT DOCUMENTS

| | | |
|---|---|---|
| KR | 20190059100 | 5/2019 |
| KR | 102104328 | 4/2020 |
| WO | 2003/005949 | 1/2003 |

OTHER PUBLICATIONS

Australian Examination Report 2, Dated Oct. 21, 2022. For related Australian Patent Application #2021221700, 4 Pages.
Extended European Search Report and Written Opinion in related Application 22859664.9-1102 / 4391981 PCT/ AU2022051004 mailed Nov. 19, 2024, 7 pages.

* cited by examiner

FRONT　　　　　　　BACK　　　　　　　SIDE

BODY FLUID MANAGEMENT INSERTS AND GARMENTS

CROSS-REFERENCE TO RELATED APPLICATIONS

The present application is the U.S. National Stage of International Patent Application No. PCT/AU2022/051004, filed Aug. 25, 2022, which enjoys the benefit of priority from the prior Australian Patent Application No. 2021221700 (filing date: Aug. 25, 2021), the entire disclosures of which are incorporated herein by reference.

TECHNICAL FIELD

The present invention relates to inserts for garments for managing body fluid discharged by a wearer. The invention further relates to garments for managing body fluid discharged by a wearer.

BACKGROUND

Unintentional body fluid discharge, such as menstrual discharge, bladder leakage, liquid faecal discharge, breast milk leakage and sweat, is an issue that many people contend with. It often results in visible stains and damage to their outer garments, causing embarrassment, especially when the discharge is associated with an odour.

Conventional leak protection products suffer from several shortcomings. Often, the absorptive capacity is often insufficient in heavy flow situations resulting in leakage. In addition, many are disposable products that require frequent replacement, become costly over time, and are bad for the environment. Furthermore, conventional products are typically bulky, uncomfortable and not sufficiently discreet.

Many prior leak protection products also include synthetic antibacterial chemical additives, implement bonding/adhesive compounds in their construction, or are chemically treated to improve absorbency. As leak prevention products are typically placed close to or directly on skin, the inclusion of such synthetic additives and compounds is not desirable, as they may become harmful/toxic to the wearer, particularly if the product is worn for longer periods, or located in a sensitive area, like around the genitals. For example, studies have shown that many disposable sanitary pad products can release volatile organic compounds and phthalates, which can be harmful to a wearer, and, due to the proximity of these products to the vaginal area when worn, where the skin is thinner, there can be absorption/uptake of these compounds at a harmful level.

'Period underwear', which is typically washable, has sought to address some of these issues. However, products to date have issues containing larger leakage volumes, and also typically include potentially toxic/harmful adhesives in their construction, in order to maintain leak prevention performance. These 'period underwear' products also typically suffer problems with leakage at the leg openings.

Due to the above deficiencies with conventional/exiting products, wearers, and particularly those with heavy menstrual flow, are often forced to use multiple products at the same time, which exacerbate the already present issues with comfort and concealment (i.e. discreetness). For example, some wearers are forced to wear period underwear in combination with a sanitary pad product and/or a tampon etc.

The present invention seeks to address the deficiencies of prior leak protection products.

The reference in this specification to any prior publication (or information derived from it), or to any matter which is known, is not, and should not be taken as, an acknowledgement or admission or any form of suggestion that that prior publication (or information derived from it) or known matter forms part of the common general knowledge in the field of endeavour to which this specification relates.

SUMMARY

In one broad form, the present invention provides an insert for a garment. The insert comprises: a liquid barrier layer having a wearer-facing side; and an absorbent layer disposed adjacent to the wearer-facing side of the liquid barrier layer. The absorbent layer covers a portion of the wearer-facing side of the liquid barrier layer but leaves at least a portion of a peripheral region of the wearer-facing side uncovered.

In some forms, the absorbent layer has a wearer-facing side and is the first of a plurality of absorbent layers of the insert, the other of the plurality of absorbent layers being stacked outwardly from the wearer-facing side of the first absorbent layer. In some forms, at least one of the plurality of absorbent layers, being one that has a neighbouring absorbent layer at its wearer-facing side, has a portion of a peripheral region of its wearer-facing side not covered by the neighbouring absorbent layer. In some forms, each absorbent layer that has a neighbouring absorbent layer at its wearer-facing side has a portion of a peripheral region of its wearer-facing side not covered by the neighbouring absorbent layer.

In some forms, the portion of the peripheral region of the liquid barrier layer that is left uncovered by the absorbent layer adjacent thereto extends along the whole perimeter of the wearer-facing side of the liquid barrier layer. In some forms, the portion of the peripheral region that is left uncovered by the absorbent layer adjacent thereto extends along a portion of the perimeter of the wearer-facing side of the liquid barrier layer.

In some forms, the insert is shaped to fit within a crotch region of an undergarment, and the portion of the peripheral region of the liquid barrier layer that is left uncovered by the absorbent layer adjacent thereto comprises the lateral sides of the liquid barrier layer, that extend between a front and rear of the insert.

In some forms, the one or more absorbent layers comprise a microfibre fabric layer. In some forms, the microfibre fabric comprises polyester and polyamide fibres with a linear mass density in the range from 0.45 denier to 1.20 denier. In some forms, the one or more absorbent layers comprise bamboo. In some forms, the one or more absorbent layers comprise a blend of bamboo and cotton. In some forms, the one or more absorbent layers formed of bamboo or a blend of bamboo and cotton have a fabric weight in the range from 250 to 400 grams per square metre.

In some forms, the liquid barrier layer is the first of a plurality of liquid barrier layers of the insert, the other of the plurality of liquid barrier layers being stacked outwardly from an out-facing side of the first liquid barrier layer, that is opposite the wearer-facing side. In some forms, the insert includes two liquid barrier layers.

In some forms, the insert comprises a second and third liquid barrier layer, the second liquid barrier layer being sandwiched between the first and third liquid barrier layers, and having a smaller size than the first and third liquid barrier layers, such that a space is provided between the first and third liquid barrier layers, at a portion of a peripheral region thereof, into which the second liquid barrier layer does not extend.

In some forms, the liquid barrier layer(s) comprises a polymer film layer and a fabric layer disposed adjacent to the polymer film layer. In some forms, the polymer film layer is a polyurethane layer. In some forms, the fabric layer of the liquid barrier layer is knitted or woven. In some forms, the fabric layer comprises a polyester knitted fabric.

In some forms, the insert is shaped to fit within a crotch region of an undergarment, and the grains of the fabric layer of at least one of the liquid barrier layers are oriented to encourage liquid travelling there-along in a direction to the front or to the rear of the insert, rather than to the lateral sides of the insert. In some forms, the straight grain of the fabric layer is aligned to run in a direction from front to rear of the insert.

In some forms, the insert comprises a second liquid barrier layer disposed adjacent to the out-facing side of the first liquid barrier layer, wherein the fabric layer of the first liquid barrier layer is disposed on the out-facing side of the first liquid barrier layer, and wherein the fabric layer of the second liquid barrier layer is disposed on the wearer-facing side of the second liquid barrier layer. In some forms, the fabric layer of the first liquid barrier layer is disposed on the out-facing side of the first liquid barrier layer, and the fabric layers of a second and third liquid barrier layers are disposed on the wearer-facing sides of the second and third liquid barrier layers. In some forms, opposite fabric layers of adjacent liquid barrier layers are arranged to permit airflow therebetween In some forms, the insert is shaped to conform to a crotch region of an undergarment, the insert comprising a middle section configured to be located between the thighs of the wearer, and front and rear sections extending from the middle section. In some forms, the width between lateral sides of the middle section is smaller for the absorbent layer(s) than for the liquid barrier layer(s). In some forms, the width between lateral sides of the middle section decreases progressively for each absorbent layer in the direction towards the wearer.

In some forms, the insert is shaped to conform to an armpit region of an upper body undergarment. In some forms, the insert is shaped to conform to a cup of a brassiere. In some forms, the insert is shaped to conform to a crotch region of pants, short pants, or nappies or diapers, the insert comprising a middle section configured to be located between the thighs of the wearer, and front and rear sections extending from the middle section.

In some forms, two or more of the layers are secured together by stitching. In some forms, any stitching between the absorbent layers and the first liquid barrier layer penetrates through the first liquid barrier layer to an interfacing region between the first liquid barrier layer and another liquid barrier layer disposed adjacent to the out-facing side of the first liquid barrier layer without extending into the other liquid barrier layer.

In some forms, any stitching between the absorbent layer(s) and the liquid barrier (s) layer is substantially spaced from the side edges of the insert.

In some forms, the insert is launderable.

In another broad form, the present invention provides a garment comprising an insert as described above.

In some forms, the garment is one of underpants, a shirt, a singlet, pants, short pants, a nappy, and a brassiere.

In some forms, the insert is positioned on a wearer-facing side of a fabric layer of the garment. In some forms, the fabric layer is the innermost layer of the garment when the garment is worn. In some forms, the fabric layer is the sole fabric layer of the garment. In some forms, the garment is underpants, wherein the fabric layer comprises a left leg opening and a right leg opening, the underpants further comprising: a first strip of liquid-impermeable, elastic fabric lining the left leg opening in the fabric layer; and a second strip of liquid-impermeable, elastic fabric lining the right leg opening in the fabric layer.

In some forms, the insert is positioned between two fabric layers of the garment. In some forms, the two fabric layers are an inner fabric layer and an outer fabric layer, the inner fabric layer being interposed between the outer fabric layer and the body of a wearer of the garment when the garment is worn, wherein the absorbent layer(s) is/are disposed at the inner fabric layer facing side of the insert and the liquid barrier layer(s) is/are disposed at the outer fabric layer facing side of the insert. In some forms the inner fabric layer is moisture wicking.

In some forms, the garment is underpants, wherein each of the inner fabric layer and the outer fabric layer comprises a left leg opening and a right leg opening. The underpants further comprise: a first strip of liquid-impermeable, elastic fabric lining the left leg opening in the inner fabric layer; a second strip of liquid-impermeable, elastic fabric lining the left leg opening in the outer fabric layer; a third strip of liquid-impermeable, elastic fabric lining the right leg opening in the inner fabric layer; and a fourth strip of liquid-impermeable, elastic fabric lining the right leg opening in the outer fabric layer.

In some forms, the garment is launderable.

In another broad form, the present invention provides a layer arrangement for leak prevention in a garment or an insert for a garment. The layer arrangement comprises two liquid barrier layers that each comprise a polymer film layer and a fabric layer. In some forms, the liquid barrier layers are arranged such that the fabric layers thereof face one another. In some forms, the liquid barrier layers are arranged such that the polymer film layers thereof face one another. In some forms, the liquid barrier layers are arranged such that the fabric layer of one of the liquid barrier layers faces the polymer film layer of the other of the liquid barrier layers.

In some forms, the layer arrangement further includes one or more absorbent layers. In some forms, the polymer film layer is waterproof and breathable. In some forms, the polymer film layer is a polyurethane membrane. In some forms, the fabric layer is a knitted fabric. In some forms, the fabric layer is a polyester knit fabric.

In another broad form, the present invention provides an insert for a garment or a garment comprising a layer arrangement as described above. In some forms the insert is configured for inclusion at the crotch region of an undergarment.

BRIEF DESCRIPTION OF THE DRAWINGS

Some embodiments of the present invention are described below, by way of example only, with reference to the accompanying drawings, in which.

DETAILED DESCRIPTION

Figure 1:
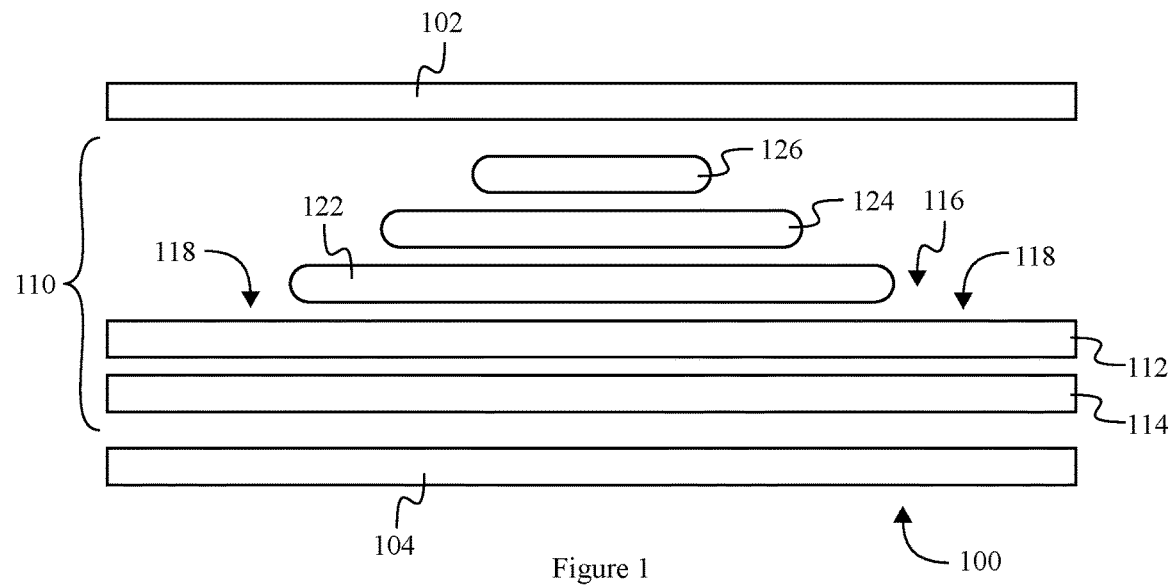
FIGS. 1 to 17 are cross-sectional views of undergarments at the crotch region including example inserts for managing body fluid discharged by a wearer of the garment.

Embodiments of the invention provide an insert for a garment for assisting with management of body fluid discharged by a wearer. The management of body fluid provided by the insert may include, for example, absorbing, containing, retaining, and/or concealing discharged body fluid, acting as a dam or providing a sand-bag type effect so as to block or obstruct the progression of discharged body fluid to an external layer of the garment. The management of body fluid may also include minimising odour from body fluids that are retained by the insert. The insert and/or a garment including same may be utilised, for example, in the management/capture of discharged menstruation fluid or urine. Typically, the insert and any garments including same are launderable i.e. made from fabrics/materials that can be washed dried and worn again without any significant deterioration to the absorptive and/or leakproof functionality of the insert/garment. That is, the insert and garments including same are typically not disposable or 'single use' type products. Also, in preferred forms, the insert is constructed without the use of potentially harmful/toxic adhesive/glues, or any heat fusing processes. In further preferred forms, the insert utilises natural fibres with inherent/natural antibacterial properties, rather than the inclusion of synthetic antibacterial compositions.

Inserts may be shaped/configured for any type of garment or clothing article. Garments may include overgarments and undergarments. For example, inserts may be configured for and implemented in undergarments to be worn under other clothes, in contact with the wearer's skin, such as briefs, underpants, knickers, a nappy, a singlet, or brassieres. In other examples, insert may be implemented in a swimming costume or swimsuit. In other examples, inserts may be implemented in overgarments likes pants, tights or short pants.

Accordingly, it will be appreciated that insert may be shaped and sized depending on the kind of garment in which it is implemented, and area of the garment in which leak protection required. Body fluid managed by the insert or garment including same may therefore be any kind of liquid or flowable material produced and released/discharged or excreted by the wearer's body, including menstruation discharge, blood, urine, flowable faecal matter, sweat, perspiration, lactation discharge, or milk. The kind of body fluid managed by the insert typically depends on the type of garment in which the insert it is implemented and where insert is located on the wearer's body.

The insert comprises a liquid barrier layer having a wearer-facing side and an absorbent layer disposed adjacent to the wearer-facing side of the liquid barrier layer. The absorbent layer covers a portion of the wearer-facing side of the liquid barrier layer but leaves at least a portion of a peripheral region of the wearer-facing side uncovered. By leaving a portion of the wearer-facing side of the liquid barrier layer uncovered, any fluid discharge (e.g. menstruation fluid) which escapes the absorbent layer to that portion of the peripheral region is more exposed to air flow, and may solidify (or partially solidify, for example, by forming a gel, etc.) or dry more quickly. Once dried, solidified, or partially solidified, the discharge (e.g. menstruation fluid) may enhance fluid management capability of the insert/garment, by providing a supplementary naturally forming seal or barrier.

In some examples, the portion of the peripheral region of the liquid barrier layer that is left uncovered by the absorbent layer adjacent thereto extends along the whole perimeter of the wearer-facing side of the liquid barrier layer. In other examples, the portion of the peripheral region of the liquid barrier layer that is left uncovered by the absorbent layer adjacent thereto extends along one or more portions of the perimeter of the wearer-facing side of the liquid barrier layer. For example, in the case of a leak proof insert configured for location at a crotch region of an undergarment for use in menstruation management, the uncovered peripheral region may extend only along the lateral sides of the insert/crotch region of the garment (i.e. adjacent the thighs of a wearer when worn) or all the way around the insert.

Typically, the liquid barrier layer is substantially liquid-impermeable, so as to substantially block or impede the passage of liquid therethrough. It will be appreciated that in some cases the liquid barrier layer may be strictly liquid impermeable so that passage of liquid is completely prohibited. In other cases, the liquid barrier layer may substantially block or impede liquid passage therethrough allowing passage of only a negligible amount liquid when compared to the amount blocked. The liquid barrier layer (and remainder of the insert) is typically breathable (i.e. permitting moisture vapour transmission) and/or air permeable to improve comfort for the wearer.

In some examples, the liquid barrier layer comprises a polymer film layer, and a fabric layer. In some examples, the polymer film layer is typically waterproof and breathable, and in some examples, comprises a polyurethane membrane. In some examples, the polymer film layer has a thickness of less than about 0.02 mm. The fabric layer may have some fluid absorbing capability and is typically a knitted or woven fabric, such as, for example, a polyester knit fabric.

The absorbent layer is typically configured to absorb, diffuse, and/or wick liquid. In some examples, the absorbent layer comprises a microfibre fabric layer. In some examples, the microfibre fabric comprises polyester and polyamide fibres. In some examples, the absorbent layer has linear mass density in the range from about 0.45 denier to about 1.20 denier. In some preferred examples, the absorbent layer comprises bamboo or a blend of bamboo and cotton.

In some examples, the absorbent layer comprising bamboo or a blend of bamboo and cotton has a fabric weight in the range from about 250 to about 400 grams per square metre. Including cotton typically provides improved breathability. In some examples, the absorbent layer is formed of inherently antibacterial materials which have not been chemically treated.

As would be appreciated, the absorbent layer also has a wearer-facing side. In some examples, the absorbent layer is the first of a plurality of absorbent layers of the insert, the other of the plurality of absorbent layers being stacked outwardly from the wearer-facing side of the first absorbent layer. In some examples, at least one of the plurality of absorbent layers, being one that has a neighbouring absorbent layer at its wearer-facing side, has a portion of a peripheral region of its wearer-facing side not covered by the neighbouring absorbent layer. In some examples, each absorbent layer that has a neighbouring absorbent layer at its wearer-facing side has a portion of a peripheral region of its wearer-facing side not covered by the neighbouring absorbent layer. It will be appreciated that the absorbent layer furthest from the liquid barrier layer does not have a neighbouring absorbent layer at its wearer-facing side and its wearer-facing side is therefore not covered by any absorbent layer.

In the same way escaped fluid discharge may dry/solidify more readily at any exposed peripheral portion of the liquid barrier layer, it may also dry/solidify more quickly at the uncovered peripheral portions of the absorbent layers, to thereby promote the formation of a supplementary seal or barrier in these areas too. Again, this may further enhance the fluid management capabilities of the insert and/or garment including same. Furthermore, the uncovered peripheral regions of each absorbent layer may extend all the way around that layer, or just along one or more portions of the periphery. In the case of a leak proof insert configured for location at a crotch region of an undergarment garment for use in menstruation management, the uncovered peripheral regions of each absorbent layer may extend along the lateral sides of the insert (i.e. adjacent the thighs of a wearer when worn) thereby providing a stepped narrowing or tapering of absorbent layers, with each absorbent layer (in the direction of the wearer) decreasing in width. This has the added benefit of being less bulky for the wearer, and minimising chaffing at the inner thighs.

Having more absorbent layers increases the absorption capacity of the insert. For instances of significant fluid discharge, such as when applied for heavy flow bleeding during menstruation (i.e. >25 ml), 2 or more absorbent layers are typically preferred.

The liquid barrier layer may also be the first of a plurality of liquid barrier layers of the insert, the other of the plurality of liquid barrier layers being stacked outwardly from an out-facing side of the first liquid barrier layer that is opposite the wearer-facing side. Preferably the insert includes at least two liquid barrier layers. For instances of significant fluid discharge, such as heavy flow bleeding during menstruation, 3 or more layers may be suitable.

In one particular example, the insert may comprise a second and third liquid barrier layer. The second liquid barrier layer typically being sandwiched between the first and third liquid barrier layer. The second liquid barrier layer may have a smaller size (or cover a smaller surface area) than the first and third liquid barrier layers such that a space is provided between the first and third liquid barrier layers at a portion of a peripheral region thereof into which the second liquid barrier layer does not extend.

It will be appreciated that the number of liquid barrier layers is selected in accordance with the application for the insert/garment, with more liquid barrier layers improving leak prevention and less typically providing improved breathability and/or air permeability to improve comfort for the wearer.

Alternatively or additionally to the leak prevention/fluid management constructions described above, leak prevention may be facilitated by the layer arrangement/orientation of the liquid barrier layers. In particular, providing two (or more) liquid barrier layers provides improved leak prevention performance. Typically, each liquid barrier layer comprises a polymer film layer and a fabric layer. In such cases, having two liquid barrier layers which are arranged such that the fabric layers thereof face one another provides especially improved leak prevention performance. Furthermore, the liquid barrier layers are typically arranged to permit airflow therebetween, which encourages any liquid received therebetween to more readily dry/solidify, instead of flowing to the peripheries to escape.

In one example, the insert is shaped to conform to a crotch region of underpants or the like, the insert comprising a middle section configured to be located between the thighs of the wearer, and front and rear sections extending from the middle section. The width between lateral sides of the middle section is typically smaller for the absorbent layer(s) than for the liquid barrier layer(s) exposing peripheral regions of the first or initial liquid barrier layer at the wearer facing side thereof. In addition, the width between lateral sides of the middle section also decreases progressively for each absorbent layer in the direction toward the wearer. This provides a stepped/pyramidal type stacking of the layers, such that the width at the middle section narrows or tapers with each layer towards the wearer. In addition to contributing to the leak proof functionality of the underpants, this stepped/pyramidal type structure at the middle section reduces bulkiness, chaffing and skin irritation between the thighs of wearer of the underpants.

In other examples, the insert may be shaped to conform to an armpit region of an upper body undergarment, or to a cup of a brassiere.

Generally, some or all of layers of the insert are secured together by stitching, and a leakproof sealant (typically non-toxic) may be applied over any stitching holes if required. The use of stitching, as opposed to adhesives or heat fusing of the layers, negates the need for the inclusion of chemicals/compositions that may become harmful/toxic to the wearer. In some examples, no adhesives are used for securement of the layers. In some examples, only stitching is used. It will be appreciated that in some examples adhesives may be used, but these are typically implemented only when they do not have a risk harming the user (e.g. when their composition is inherently non harmful/non-toxic). For securement within a garment, the insert is also typically stitched, typically around its outer peripheral edge.

The location of the stitching between the one or more absorbent layers, and initial liquid barrier layer (i.e that which is adjacent the absorbent layers) is also typically such that it contributes to the leakproof functionality of the insert (or garment including same). Typically, the stitching between the one or more absorbent layer/s and the initial liquid barrier layer is or is mostly spaced from the peripheral edges of the liquid barrier layer (preferably by at least about 15 mm). This provides that any seepage through the stitching is distanced from the edges of the insert, and less likely to flow to the edges, where there is typically a higher risk of leakage. For example, when the insert is configured for the crotch region of an undergarment, stitching of the absorbent layer(s) to the initial liquid barrier layer is typically inset at least from the lateral sides of the middle section of the insert, such that any seepage therethrough is distanced from the leg openings of the garment (where the liquid barrier layer(s) is/are typically stitched to the garment and where there is accordingly a higher risk of leakage). In some cases, in the middle section, the stitching may travel along the side peripheries of one or more of the absorbent layers, which are inset from the side edges of the liquid barrier layer.

Furthermore, in the instance where there may be multiple liquid barrier layers, the stitching of the absorbent layers is generally only to the initial liquid barrier, and does not puncture/penetrate the second liquid barrier layer onwards. This avoids any seepage via stitching through all the liquid barrier layers, with any seepage/liquid typically contained between the first and second liquid barrier layers. However, in certain forms, such as those designed for heavy flow/bleeding during menstruation (e.g. >25 ml), which may have three liquid barrier layers or more, the stitching may penetrate more of the liquid barrier layers such that the insert/garment is more robust. However, it will be appreciated the stitching from the absorbent layers will never penetrate the ultimate or bottom liquid barrier layer. For example, in a form with three liquid barrier layers, the stitching may penetrate the first two liquid barrier layers, but not the third outermost liquid barrier layer.

It will be appreciated that embodiments of the invention are also provided by garments including the inserts as described herein. Such garments may be, for example, underpants, shirts, singlets, pants, short pants, nappies, or brassieres. It will be appreciated that the insert is typically positioned between two fabric layers of the garment. The two fabric layers typically being an inner fabric layer and an outer fabric layer, the inner fabric layer being interposed between the outer fabric layer and the body of a wearer of the garment when the garment is worn. It will be appreciated that the absorbent layer(s) is/are typically disposed at the inner fabric layer-facing side of the insert and the liquid barrier layer(s) is/are typically disposed at the outer fabric layer facing side of the insert.

When embodied in an undergarment, the inner layer is typically located against the wearers skin, and is thus also typically configured to be moisture wicking so as to facilitate fluid/liquid transfer to the absorbent layers keeping the wearer dry and comfortable. Also, as the one or more absorbent layer/s essentially space the inner fabric layer of the garment from the initial liquid barrier layer, there is typically reduced or limited contact between the inner fabric layer and the uncovered peripheral regions of the liquid barrier layer, such that discharged fluid transfer directly to the liquid barrier layer is not facilitated. Instead, discharged fluid is preferentially drawn into the top-most absorbent layer, which has high absorptive properties and is in direct contact with the inner fabric layer. Furthermore as some or all of the top most absorbent layer is typically inset from the edges of the liquid barrier layer (s), it helps to pull or draw discharged fluid away from the edges of the insert, again minimising the risk of leakage and contributing to the leak proof functionality of the garment.

In other forms, the insert may be positioned on or adjacent to a wearer-facing side of a fabric layer of the garment, which is the sole fabric layer of the garment, or the inner-most layer of the garment (i.e. the layer of the garment configured to be disposed nearest to the wearer's body when the garment is worn). In this way, no other fabric layer of the garment is located between the wearer's body and the insert. For example, in cases in which the garment comprises a single, or no more than one, fabric layer, the insert may be disposed on the wearer-facing side of that fabric layer. In such cases, the insert may comprise an additional top cover layer, over the absorbent layers, that is configured as a fluid acquisition layer to wick discharged liquid into the absorbent layers, where it is to be retained. The top cover layer may for example be formed of inherently antibacterial materials which have not been chemically treated.

It will be appreciated that that when implemented in a garment, the insert may not be an 'insert' as such, but integrally and irremovably formed/manufactured within the garment at an area thereof that requires leakproof capability. It will also be appreciated that whilst the inserts and garments including same as described herein are typically configured to be launderable/non-disposable products, in some forms, the inserts and garments including same as described herein (or any aspects thereof) may be embodied in or adapted as/for a disposable type product.

Some particular examples of the inserts and garments including same are now described with reference to the figures.

Figure 43:
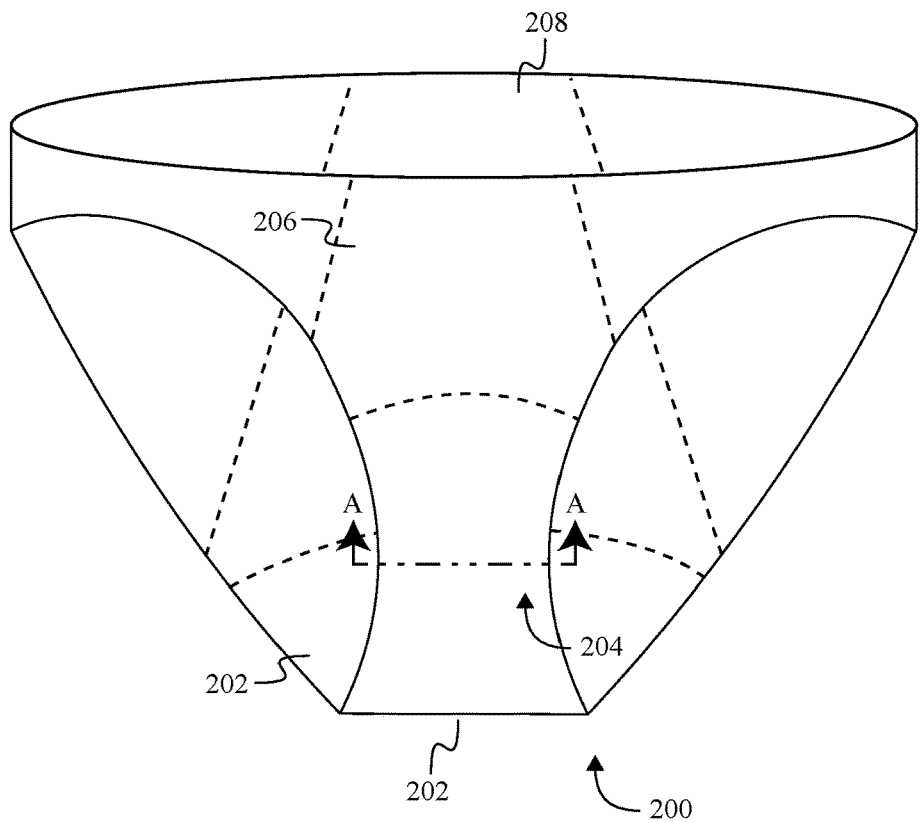
FIG. 43 is front view of an example pair of male or female underpants.
Figure 44:
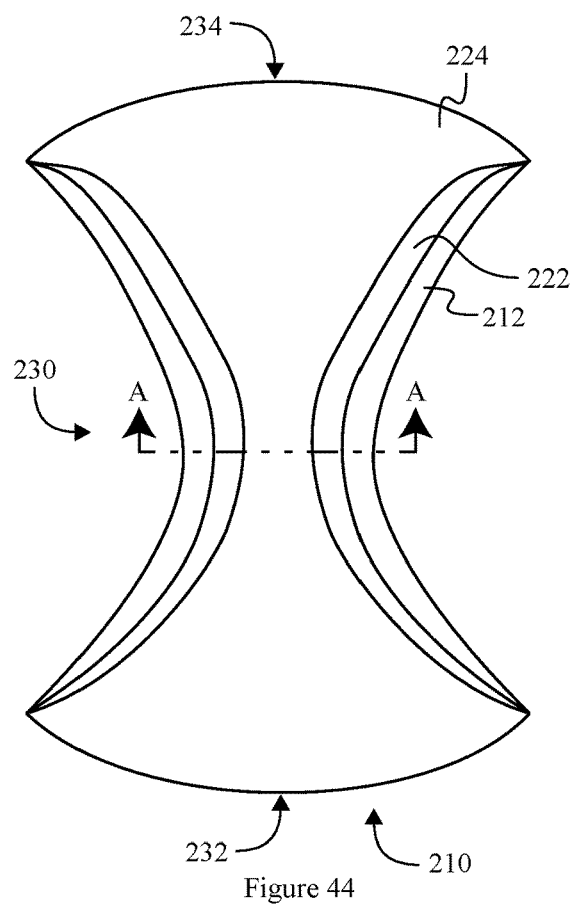
FIG. 44 is a top view of an example insert for managing body fluid shaped to conform to a crotch region of an undergarment.

FIG. 1 to 17 illustrate schematic cross sections of inserts according to the invention at a crotch region or gusset between leg openings of an undergarment. A general indication as to the location of the cross sections is illustrated by lines A-A of FIGS. 43 and 44, which illustrate a typical underpants shape, and an example insert that may be located within same. Whilst the cross sections shown in FIG. 1 to 17 are cross sections representative of a crotch region or gusset of undergarment, it will be appreciated that the layer arrangements and stepped edge profiles of the inserts as shown, may be implemented in other garments or garment areas to assist with leak prevention at other areas of the body (such as, for example, when an insert is configured for a bra cup etc.). FIGS. 19 to 25 illustrate top views of example shapes of inserts configured for the crotch region, which typically include a front and rear section, and a middle section therebetween that has concave sides to accommodate the thighs of the wearer.

FIG. 1 illustrates a cross section of a crotch region of an undergarment 100 comprising an example insert 110 for managing body fluid, e.g. blood or urine, discharged by the wearer. Again, example inserts shaped for the crotch region of an undergarment are shown in FIGS. 19 to 25.

Insert 110 is disposed between a first or inner layer 102 and a second or outer layer 104 of undergarment 100. Layers 102 and 104 are typically fabric layers. In some examples, inner layer 102 is made of natural fibres with inherent antibacterial properties. The inner layer 102 is typically moisture wicking serving as a fluid acquisition layer to transfer discharged fluid into the insert 110 improving comfort and dryness for the wearer. The inner fabric layer may be formed of, for example, hydrophilic fibres or a combination of hydrophilic and hydrophobic fibres. When garment 100 is worn, inner layer 102 is disposed between the body of the wearer and outer layer 104. That is, inner layer 102 is configured to be disposed in direct contact or adjacent to the wearer's body or skin. Outer layer 104 is the outermost layer of garment 100 and typically comprises no more than one layer of fabric, so as to minimise the profile of garment 100 and achieve a discreet appearance on the wearer's body. It will be appreciated that when the inserts as described herein are implemented in other garments, or other variations of undergarments, the garment may comprises one or more other layers in addition to the inner layer and outer layer (i.e. in addition to 102 and 104 in this example).

Insert 110 may be inserted, implanted, incorporated, embedded or integrally formed/manufactured within garment 100 between layers 102 and 104. Insert 110 is typically fixed to garment 100 by sewing in seeking to avoid the use of adhesives or hot fusion processing which sometimes require substances that later become harmful/toxic to a wearer. Whilst insert 110 is typically permanently fixed to garment 100, it may in some forms be removably secured or located therein to allow insert 110 to be selectively inserted or removed from undergarment 100.

Insert 110 is typically a launderable non-disposable item, such that any garment 100 containing same can be readily washed and re-used. Even so, when ultimately disposed, insert 110 and garment 100 may be configured to decompose, degrade, or break down in landfill, compost, soil, or recycling facilities faster than traditional disposable products (e.g. disposable sanitary pads). Furthermore, undergarment 100 comprising insert 110 is typically configured to be worn for longer periods of time than traditional disposable menstrual products, without leaking.

In the embodiment of FIG. 1, insert 110 comprises a first liquid barrier layer 112 and a second liquid barrier layer 114. In other examples, insert 110 may comprise any number, such as one or more, of liquid barrier layers.

In the embodiment of FIG. 1, insert 110 further comprises a first absorbent layer 122, a second absorbent layer 124, and a third absorbent layer 126. It will be appreciated that, in other examples, insert 110 may comprise any number, such as one or more, of absorbent layers. In some examples, insert 110 may comprise three or more absorbent layers, but usually no more than six absorbent layers.

Generally, the liquid barrier and absorbent layers comprise substantially planar bodies of material shaped to conform a desired application or to fit appropriately within a particular garment type. Example insert shapes suitable for use in the crotch region of an undergarment are shown at FIGS. 19 to 25.

It will be appreciated that the thicknesses of the layers may vary. In some examples, each liquid barrier layer has a thickness of about 0.8 mm but other thicknesses may also be suitable (e.g. 0.5 mm). It will be appreciated that the thicknesses of the liquid barrier layers may impact the leakproof/liquid retaining capability of the insert as well as the breathability/air permeability, and so certain thicknesses can be selected in accordance with a particular application (i.e. some thicknesses may be selected for improved breathability, or for heavy menstrual flow etc.)

The liquid barrier layers and the absorbent layers are provided in a stack formation (face-to-face) and are typically oriented parallel, or substantially parallel, to each other and to layers 102 and 104 of undergarment 100. Moreover, the liquid barrier layers and the absorbent layers are typically flexible to allow them to conform with changes in the shape of layers 102 and 104 that may occur when garment 100 is handled or worn, for example, due to the body shape, posture, or movement of the wearer.

Each liquid barrier layer and each absorbent layer comprises an "in-facing" or "wearer-facing" side or surface and an "out-facing" side or surface. The wearer-facing side is the major or prominent face/side of the layer configured to face the wearer when undergarment 100 is worn. The out-facing side is the major or prominent face/side of the layer configured to face away from the wearer when undergarment 100 is worn. Therefore, the wearer-facing side and the out-facing side of each layer are opposite to each other and face opposite directions. In the illustrated examples, the wearer-facing side of a layer is the top side as shown, while the out-facing side is the layer's underside.

Liquid barrier layers 112 and 114 are arranged in a stack or pile, so that the wearer-facing side of liquid barrier layer 114 is covered by liquid barrier layer 112. Liquid barrier layers 112 and 114 have the same size, so that their edges align in the stack and extend to an edge or perimeter of inner layer 102 and outer layer 104. The edge or periphery of inner and outer layers 102 and 104 typically provides the edge of the leg openings of the undergarment.

Absorbent layers 122, 124, and 126 are also arranged in a stack or pile. Absorbent layers 122, 124, and 126 have different sizes, and they are arranged in the stack in order of decreasing size in the direction of the wearer. This increases absorbent capacity without compromising comfort for the wearer. The largest absorbent layer (i.e. absorbent layer 122) is disposed at the base of the stack, adjacent to liquid barrier layer 112, giving the stack of absorbent layers a stepped or pyramidal-type edge profile. Absorbent layer 124 (i.e. the next-largest absorbent layer) is disposed adjacent to the wearer-facing side of absorbent layer 122, and covers a portion of the wearer-facing side of absorbent layer 122, while leaving at least a portion of a peripheral region of the wearer-facing side of absorbent layer 122 uncovered or exposed. Similarly, absorbent layer 126 (i.e. the smallest absorbent layer) is disposed adjacent to the wearer-facing side of absorbent layer 124, and covers a portion of the wearer-facing side of absorbent layer 124, while leaving at least a portion of a peripheral region of the wearer-facing side of absorbent layer 124 uncovered or exposed. In this way, the width of the absorbent layers between lateral sides of the insert tapers or narrows with each layer towards the direction of the wearer. The stepped/pyramidal-type edge profile of the absorbent layers allows insert 110 to contain multiple absorbent layers, thus increasing the overall absorption of insert 110, without enlarging insert 110 in a way that would cause noticeable discomfort to the wearer e.g. by causing chaffing a the inner thighs of the wearer. The step-like edge profile of the absorbent layers (which provides a sequential narrowing of the width of the absorbent layers) typically extends at least along lateral sides of insert at the middle section, but may also extend all the way around the periphery of the insert (i.e. to include the forward facing and rearward facing parts of the insert).

It will be appreciated that when referring to smaller or larger 'sizes' of layers, this relates to variation in the two-dimensional shape area, length or width (as opposed to the thickness of the layers) such that the size discrepancies between layers provide the uncovered peripheral regions. However, the thicknesses of the layers may also vary. It will also be appreciated that the layers do not have to have the same shape, but there is generally (but not always) some conformity (see e.g. FIGS. 19-25).

In some examples, the width of each absorbent layer at the narrowest part between lateral sides of the insert 110 is between 25% and 75% of the width of its larger, adjacent absorbent layer in the stack. As described the narrowing profile of the stack of absorbent layers may provide a more comfortable, ergonomic design for the wearer. However, in alternative forms, some or all of the absorbent layers may have the same size.

Absorbent layer 122 is disposed adjacent to the wearer-facing side 116 of liquid barrier layer 112 and covers a portion of wearer-facing side 116 while leaving at least a portion of a peripheral region 118 of wearer-facing side 116 uncovered or exposed. Peripheral region 118 may comprise one or more areas of wearer-facing side 116 at or near an edge, perimeter, or border of wearer-facing side 116. The uncovered portion of peripheral region 118 typically extends at least along lateral sides of the insert but may extend along or encompass the whole perimeter of wearer-facing side 116 (see for example FIGS. 19-25).

It follows that the size of absorbent layer 122 adjacent to liquid barrier layer 112 is smaller than that of liquid barrier layer 112, so that liquid barrier layer 112 extends beyond or protrudes from the perimeter or edge of absorbent layer 122 in some areas or around the whole perimeter. Peripheral region 118 may extend from the perimeter or edge of absorbent layer 122 by at least 5 mm. In some cases, peripheral region extends in the range of 10 mm to 15 mm, and in some other cases, more than 15 mm.

Figure 45:
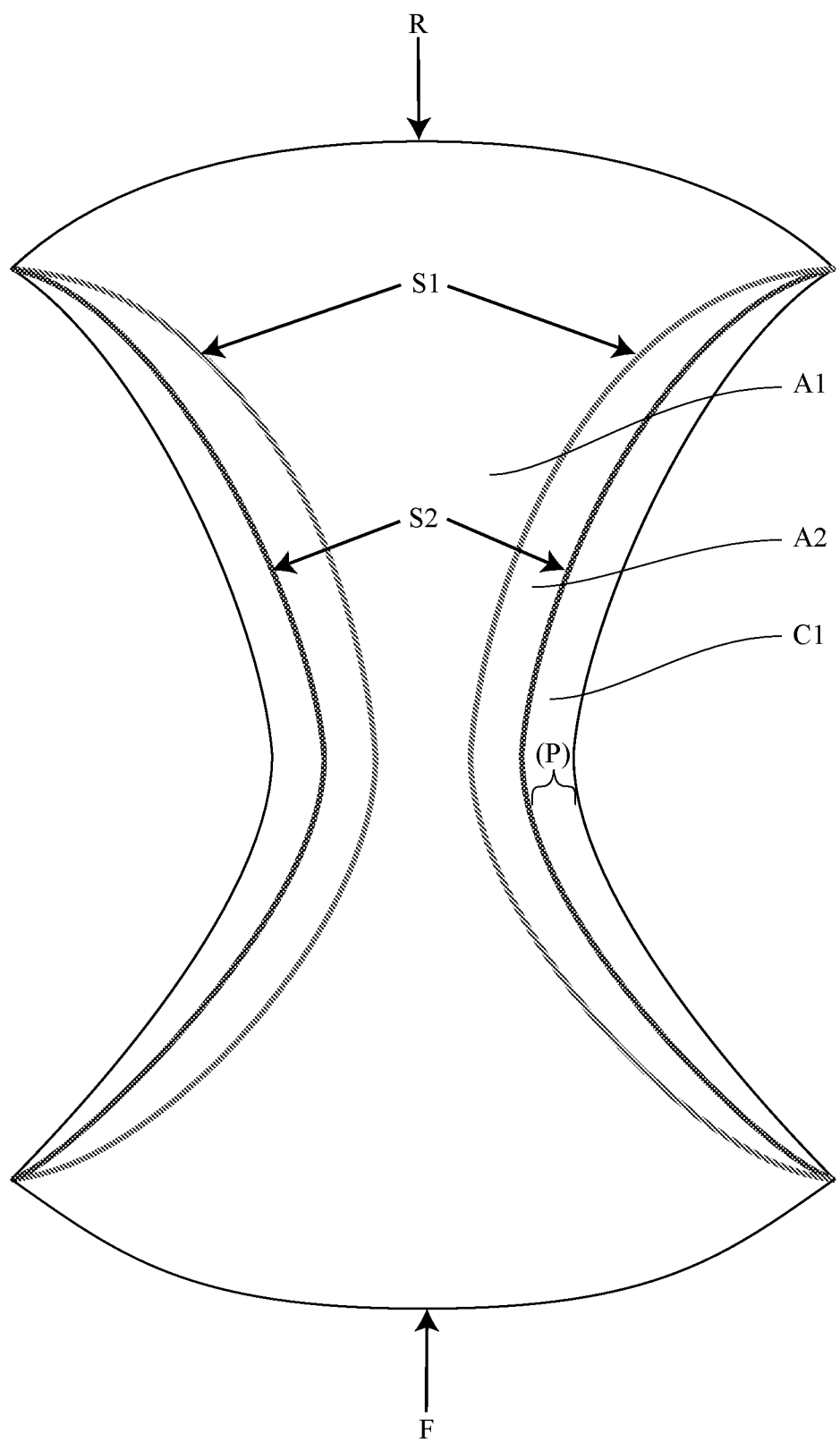
FIG. 45 is a top view of an example insert for managing body fluid shaped to conform to a crotch region of underpants showing an example of typical stitching lines for securing absorbent layers to the liquid barrier layer.

Each absorbent layer and each liquid barrier layer is typically attached or connected to its adjacent layers by stitching without the use of adhesives or hot fusion processing in seeking to avoid later degradation and release of potentially toxic substances from the adhesives or that may have been used in the hot fusion processing. In one example, at the middle section of the insert, which is typically narrowest and to be located between the thighs of the wearer, the absorbent layers are typically stitched to liquid barrier layer 112 in a central region of the insert, that is, spaced (or mostly spaced) from the concave sides of the middle section of the insert. In some examples, stitching may run along peripheral edges of absorbent layers 124 and/or 126, to secure the absorbent layers to the liquid barrier layer. As an illustrative example of typical placement of stitch lines along peripheries of absorbent layers, FIG. 45 shows stitch lines S1 and S2 running along peripheries of absorbent layers A1, A2 respectively, which are both inset from lateral sides of liquid barrier layer C1. In this example, the spacing P from the concave edge to the closest stich line S2 is greatest (typically at least 15 mm) at the middle narrow section of the insert, with P decreasing towards the front and rear of the insert following the edge of the absorbent layer A1. Typically, in embodiments like that of FIG. 45, all layers are then stitched together along the front (F) and rear edges (R) of the insert.

To prevent or reduce leakage, the liquid barrier layer nearer to or adjacent to outer layer 104 (i.e. liquid barrier layer 114 in the illustrated example) is typically not punctured by stitching with the absorbent layers.

To secure the insert within the garment, layers 112 and 114 are typically secured to inner layer 102. Typically, liquid barrier layers 112 and 114 are stitched at their outer edges to inner layer 102 so as to reduce the risk of leakage through any puncture holes (which are distanced from the centre of the insert where discharge flow is typically received). As the internal stitching to attach the absorbent layers to the first liquid barrier layer 112 is spaced (or (mostly spaced) from the edges of the insert where the fabric layer 102 and liquid barrier layers 112, 114 are attached, there is less chance of liquid that has seeped through absorbent layer stitching arriving at the edges of the liquid barrier layers where the stitching to the inner fabric layer is located. As noted above the layers are not typically stitched to the garment outer layer 104, so that, from the outside, the undergarment appears "normal" and does not include any stitch/securement lines that would indicate the presence of the insert 110 within the garment.

However, in some forms, the liquid barrier layers are alternatively or additionally stitched to the outer layer 104. Any stitches or stitching holes may be closed or covered with a sealant. In some examples, the sealant is made from polyurethane, thermoplastic polyurethanes, other suitable thermoplastic polymers, and/or other liquid-impermeable sealing materials. The sealant may be made with non-harmful chemicals according to OEKO-TEX™ standards for textiles.

Each liquid barrier layer 112, 114 is configured to block, impede, or obstruct the passage of liquid through the liquid barrier layer. In some examples, each liquid barrier layer is liquid-impermeable, liquid-impervious, or leakproof. It is to be understood that a liquid barrier layer may still be considered to block liquid if it allows the passage of a small or negligible amount of liquid through it compared to an amount of liquid blocked. In addition, each liquid barrier is typically breathable (permitting moisture vapour transmission) and/or air permeable to improve comfort for the wearer. It will be appreciated that breathability/air permeability may be variable depending on the material selected for the liquid barrier layer, and may be configured for a particular application.

In some examples, each liquid barrier layer comprises a polymer film or laminate layer, and a fabric layer. For example, the polymer film layer may be polyurethane membrane, and the fabric layer may comprise a knitted or woven fabric or cloth layer. In one example the fabric layer may comprise a liquid-holding compound fabric that possesses some fluid-absorbing capability. The polymer film layer may be disposed adjacent to, and may be attached or bonded to, the fabric layer. The polymer film layer is typically waterproof and breathable, and typically has a thickness less than about 1 mm. In some preferred examples, the polymer film layer has a thickness of less than about 0.02 mm. In some examples, the polymer film layer has thickness of about 0.016 mm, and in some examples about 0.012 mm. Example suitable knitted or woven fabric layers may have a linear mass density of about 75 denier or less, and in some preferred examples about 20 denier or less. Furthermore, example suitable knitted or woven fabric layers may have a fabric weight of about 95 gsm or less, and in some preferred examples in the range from about 40 gsm to about 50 gsm. In some examples, the woven or knitted fabric layer comprises a polyester knit fabric. In other examples, the knitted fabric layer comprises a fibre derived from cotton or a blend of polyester and cotton.

Each absorbent layer is typically configured to absorb, diffuse, or wick liquid. Each absorbent layer 122, 124, 126 may be made of a high moisture-absorbing material. In some examples, each absorbent layer comprises a microfibre fabric layer. In some examples, each absorbent layer has a linear mass density in the range from about 0.45 denier to about 1.20 denier. In some examples, the microfibre fabric may comprise polyester and polyamide fibres with a linear mass density in the range from about 0.45 denier to about 1.20 denier, which provides a highly absorbent, fast-drying microfibre fabric. In some examples, the microfibre fabric may have a fabric weight in the range from about 150 gsm to about 500 gsm. In some examples, each absorbent layer comprises a fabric made of one or more of bamboo, bamboo charcoal, hemp, cotton, organic cotton, polyester or polyamide microfibre material, or any other hydrophilic fabric. In some examples, each absorbent layer comprises a towel fabric layer. In one example, the towel fabric layer comprises bamboo or a blend of bamboo and cotton with a fabric weight in the range of about 250 to about 400 grams per square metre.

It will be appreciated that the liquid- and/or gas-management properties of each liquid barrier layer and absorbent layer are typically dependent on the properties of the layer material, layer structure, or combination thereof.

During use, the absorbent layers are configured to absorb and retain body fluid discharged by the wearer. Each additional absorbent layer may increase the absorption and fluid retention of insert 110. The absorbent layers may wick or diffuse the body fluid away from the wearer. Each absorbent layer may transport body fluid towards drier regions within the stack of absorbent layers. The liquid barrier layers may block or impede the flow of body fluid that diffuses through the stack of absorbent layers. Therefore, insert 110 holds body fluid and prevents or resists the transport of body fluid and, in some examples, microbes and odour of the body fluid, to outer layer 104 and/or to other garments of the wearer.

The arrangement of the absorbent layers and the liquid barrier layers allows for air to flow through insert 110. The securement between adjacent layers permits air flow between them, which allow air gaps/pockets to form. Even if adjacent layers are in contact with each other, they may still have residual space between them to permit airflow therethrough. Peripheral region 118 may also enhance airflow and allow air to pass through the layers. The fact that peripheral region 118 is exposed and not covered by other layers means that airflow through peripheral region 118 is not restricted by other layers. Likewise, any peripheral region of the absorbent layers (or any other layer) that is not covered by another layer, at least on one side, is better exposed to air or airflow.

Airflow through insert 110 may facilitate the drying of body fluid absorbed or contained by insert 110. In examples in which the body fluid is blood, insert 110 may facilitate coagulation of the blood at the exposed edges of the absorbent layers and/or at the exposed peripheral region of the liquid barrier layers. This is because the uncovered area at the edges of the layers are more exposed to air, which encourages the blood to harden/solidify and form a natural, supplementary seal or barrier to further deter seepage and leaking.

In typical use, discharge (e.g. menstruation fluid) would encounter the centre region of topmost absorbent layer 126 first, and from there diffuse among absorbent layers 124 and 122 below. As the discharge reaches the edges of the absorbent layers it is encouraged to dry or harden, which forms a supplementary barrier or seal, to limit or stop escape of discharge out beyond the edges. The discharge is thus centrally confined between sides of the insert (or encouraged to be) within the absorbent layers. After penetrating the absorbent layers, discharge may reach the centre region of the first liquid barrier 112, and is substantially blocked thereby, with any excess discharge progressing outwardly towards the uncovered peripheral regions 118 at the sides of the insert. Again, at the peripheral regions, due to the exposure to air flow, the discharge again dries more readily, forming a natural seal or barrier to limit or stop discharge moving there beyond to reach the edges of garment inner/outer layers 102, 104 (avoiding/minimising leakage at the leg openings). Excess discharge may also flow towards the front/back of the insert, where the absorbent layers extend. Any limited/negligible discharge that may penetrate the first liquid barrier layer 112 (e.g. through stitching holes or holes in the layer caused by the wearer's misuse) is stopped by the second barrier layer 114.

In some examples, insert 110 further comprises indicators of wetness and/or saturation of insert 110, to signal to the wearer that insert 110 or garment 100 may need to be changed. The indicators may be visual indicators, for example, whose colour changes based on the specific areas and/or layers of insert 110 that are wet or saturated with body fluid.

FIGS. 2 to 16 illustrate cross sections of some example variations of insert 110 located at the crotch region of an undergarment. The variations described herein do not represent an exhaustive set, and variations other than the ones described may be possible. As previously noted, the cross-section location is generally indicated by the line A-A in FIGS. 43 and 44 which respectively show a typical underpants garment and example insert configured for use in same. Also, as previously noted, the side edge profiles of the inserts shown in the cross sections typically extend at least along the lateral sides of the insert, but may, in some forms, extend all the way around the insert (see e.g. FIGS. 19 to 25).

Figure 2:
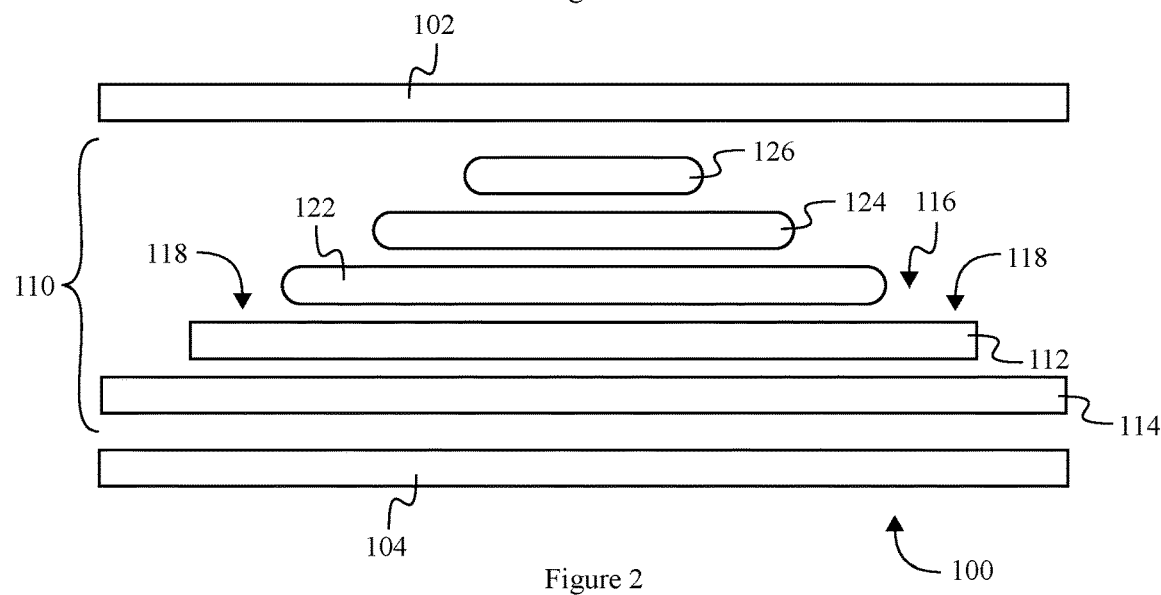
Figure 3:
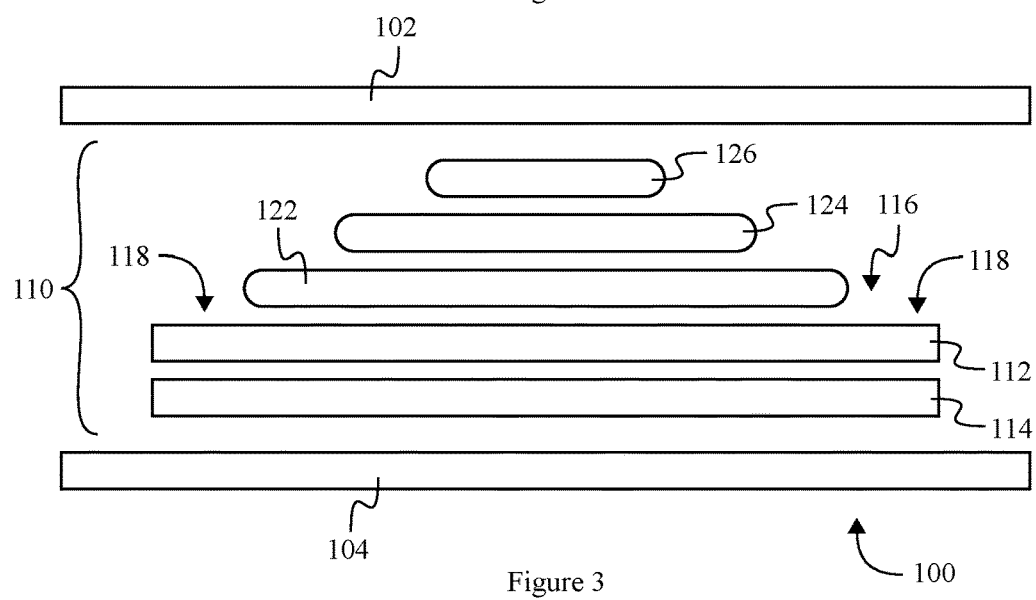

FIG. 2 illustrates an example embodiment of insert 110 in which liquid barrier layer 112 is smaller (at least across a width of the insert middle section) than liquid barrier layer 114, with liquid barrier layer 114 extending to an edge or perimeter of layers 102 and 104, and liquid barrier layer 112 spaced or set back from the edge or perimeter of layers 102 and 104, leaving at least a portion of a peripheral region of the wearer-facing side of liquid barrier layer 114 exposed or uncovered. That is, liquid barrier layer 112 is smaller (i.e. narrower in width) than layers 102 and 104, so that a gap exists between an edge or perimeter of liquid barrier layer 112 and a corresponding or nearest edge or perimeter of layers 102 and 104. FIG. 3 illustrates an example embodiment of insert 110 in which liquid barrier layers 112 and 114 have the same size and are both spaced or set back from the edge or perimeter of layers 102 and 104.

Figure 4:
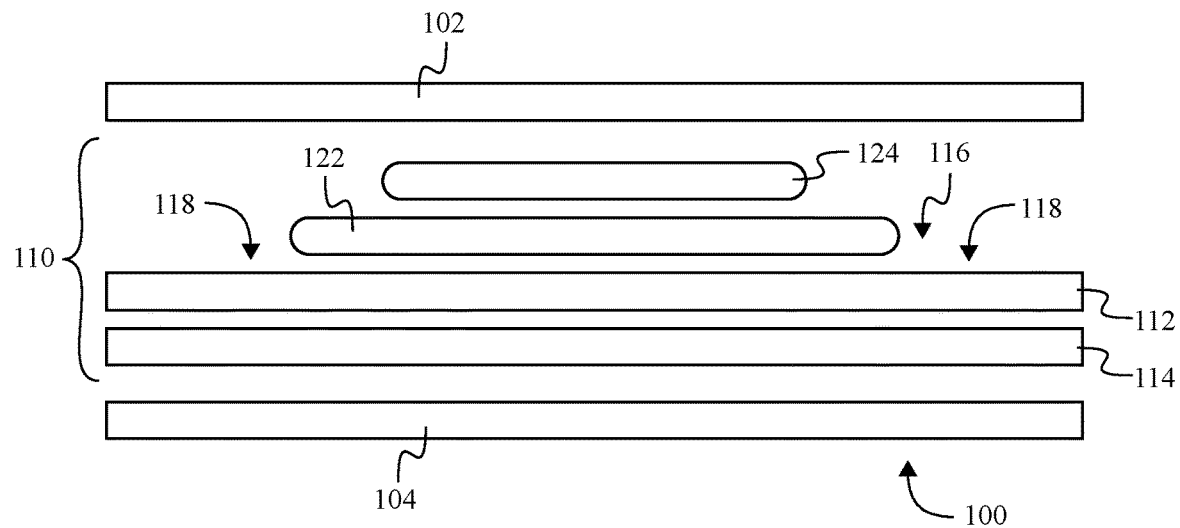
Figure 5:
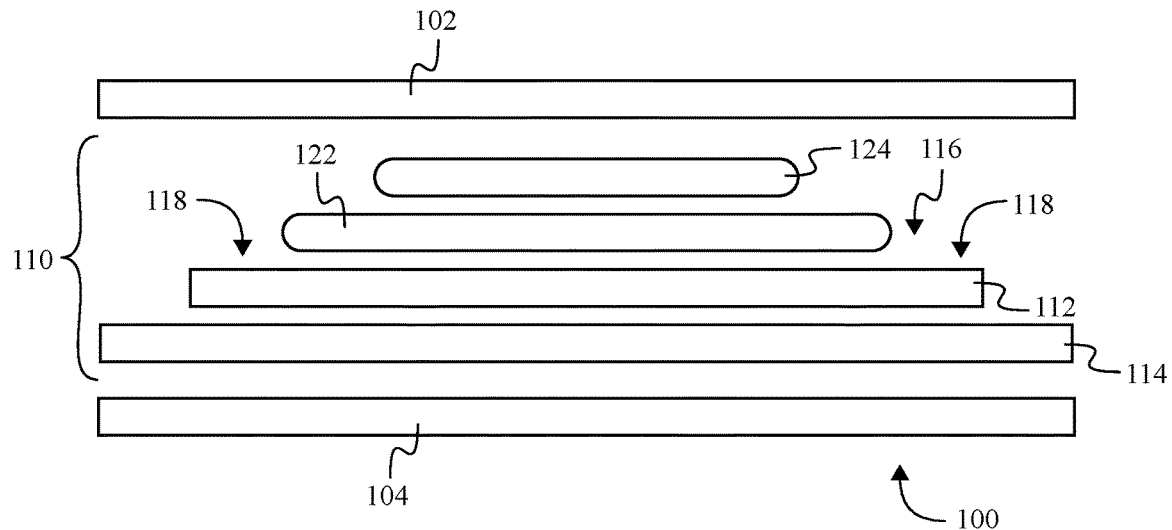
Figure 6:
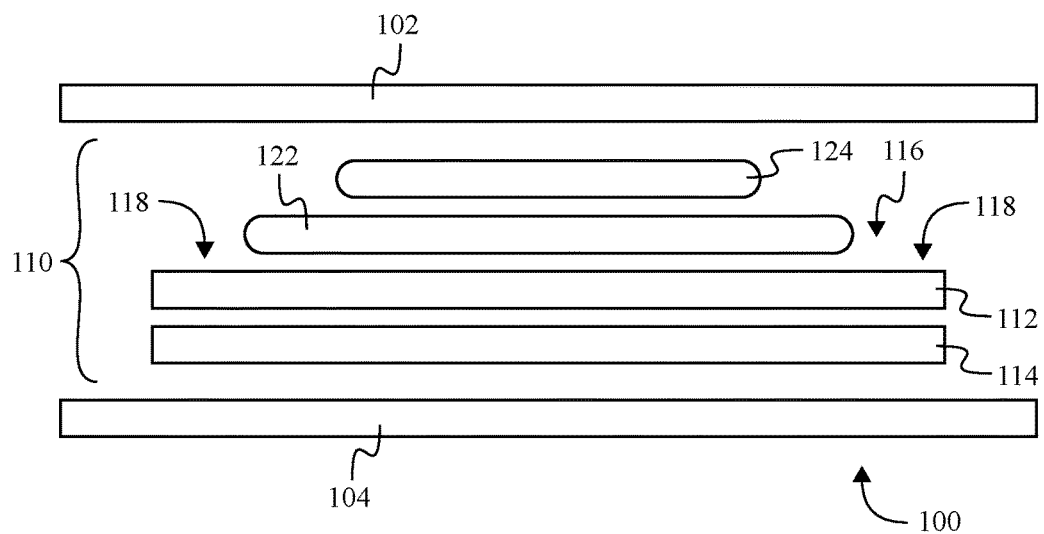

FIGS. 4 to 6 illustrate example embodiments of insert 110 comprising only two absorbent layers 122 and 124 (i.e. absorbent layer 126 is absent). In FIG. 4, liquid barrier layers 112 and 114 have the same size and extend to an edge or perimeter of layers 102 and 104. In FIG. 5, liquid barrier layer 112 is smaller (at least across a width of the insert middle section) than liquid barrier layer 114, with liquid barrier layer 114 extending to an edge or perimeter of layers 102 and 104, and liquid barrier layer 112 spaced or set back from the edge or perimeter of layers 102 and 104. In FIG. 6, liquid barrier layers 112 and 114 have the same size and are spaced or set back from the edge or perimeter of layers 102 and 104.

Figure 7:
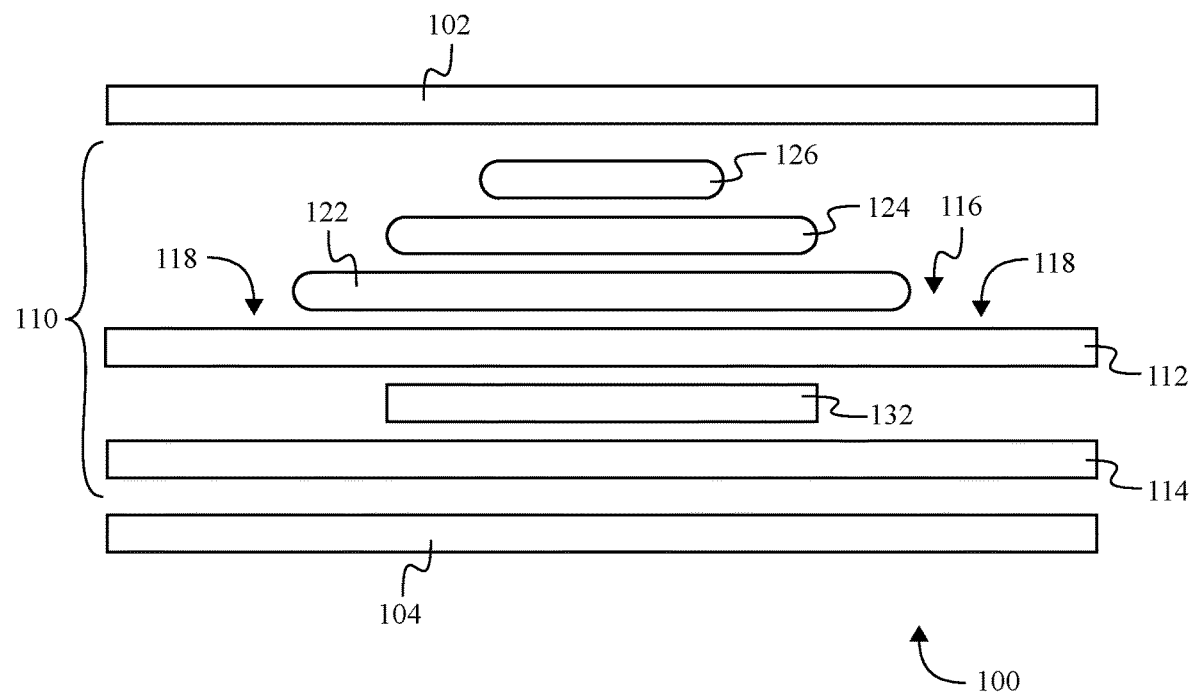
Figure 8:
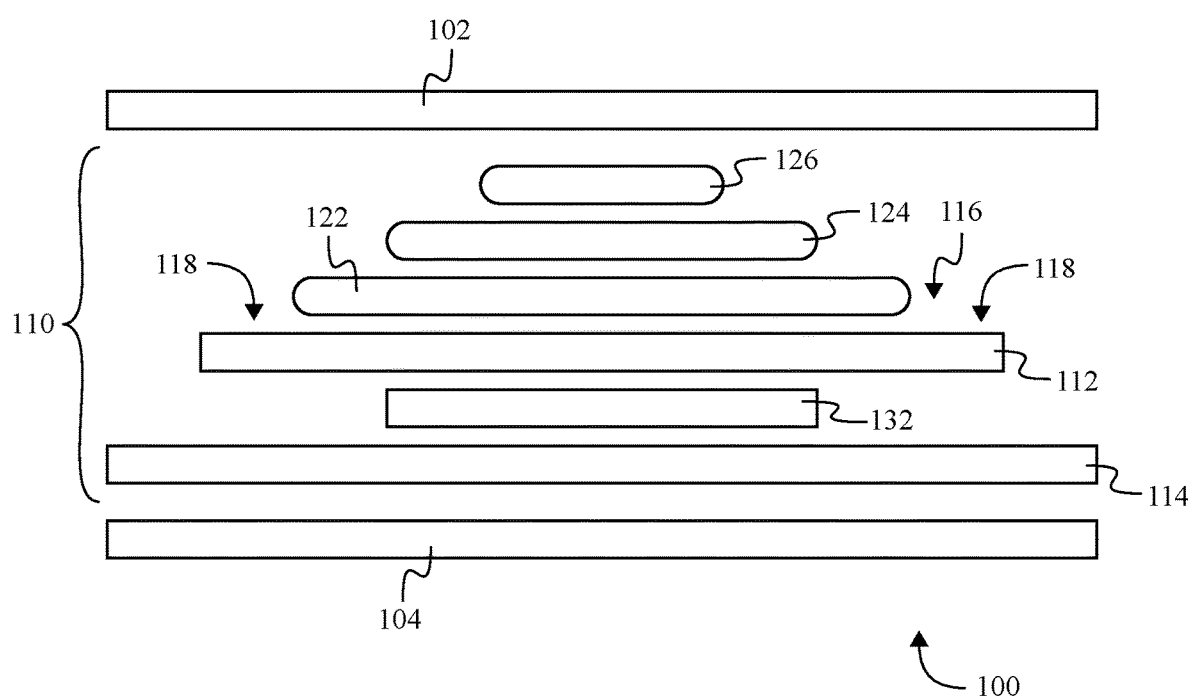
Figure 9:
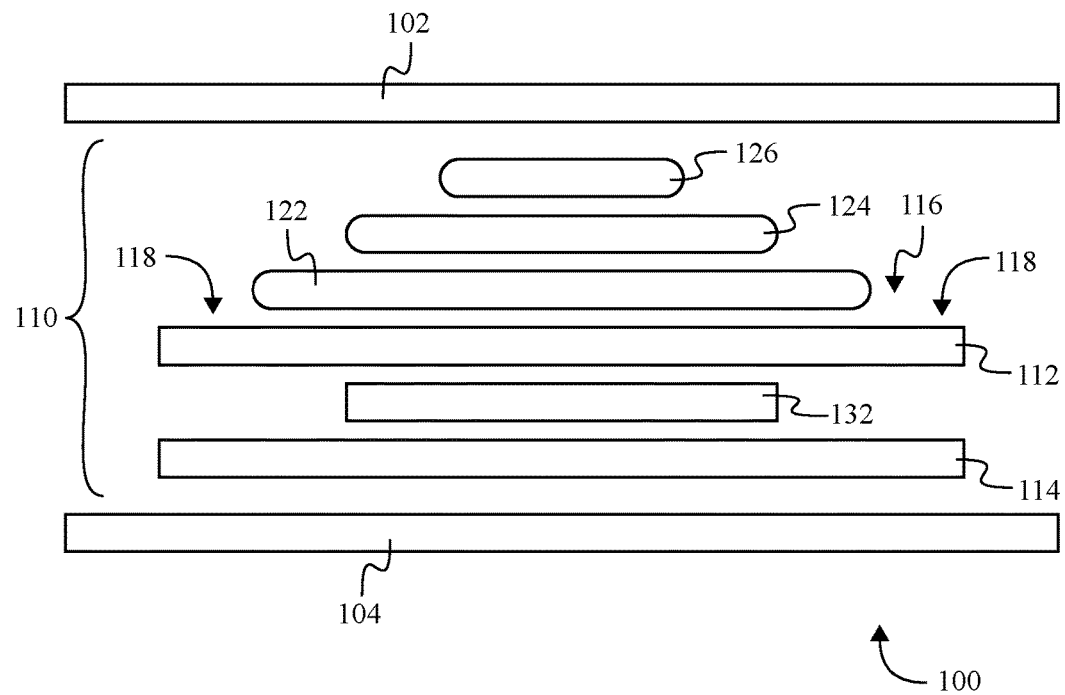

FIGS. 7 to 9 illustrate example embodiments of insert 110 comprising a third liquid barrier layer 132 disposed between liquid barrier layers 112 and 114. Liquid barrier layer 132 has a smaller size (at least across a width of the insert middle section) than liquid barrier layers 112 and 114. In particular, the area of the wearer-facing side of liquid barrier layer 132 is smaller than that of liquid barrier layers 112 and 114. Liquid barrier layer 132 is disposed at or near a central region of liquid barrier layers 112 and 114, so as to strengthen the fluid-blocking properties of insert 110 in the area expected to receive most of the body fluid discharged by the wearer. The composition of liquid barrier layer 132 may be the same or different as that of layers 112 and 114. In other examples, additional liquid barrier layers may be disposed at any other location between layers 112 and 114. In FIG. 7, liquid barrier layers 112 and 114 have the same size and extend to an edge or perimeter of layers 102 and 104. In FIG. 8, liquid barrier layer 112 is smaller (at least across a width of the insert middle section) than liquid barrier layer 114, with liquid barrier layer 114 extending to an edge or perimeter of layers 102 and 104, and liquid barrier layer 112 spaced or set back from the edge or perimeter of layers 102 and 104. In FIG. 9, liquid barrier layers 112 and 114 have the same size and are spaced or set back from the edge or perimeter of layers 102 and 104.

Figure 10:
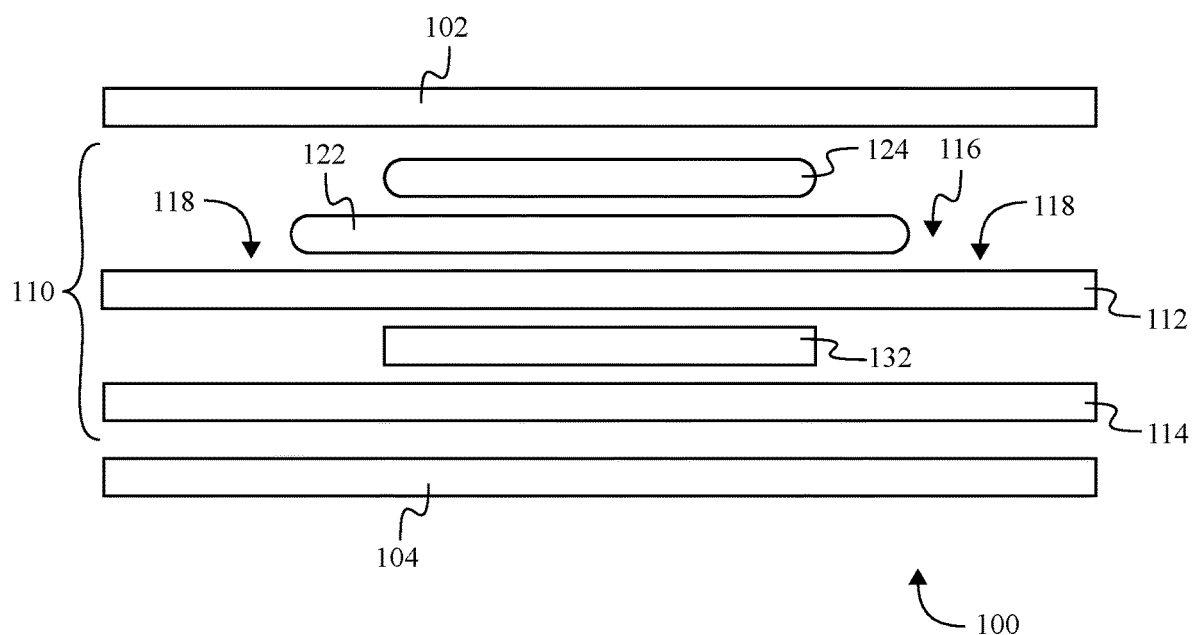
Figure 11:
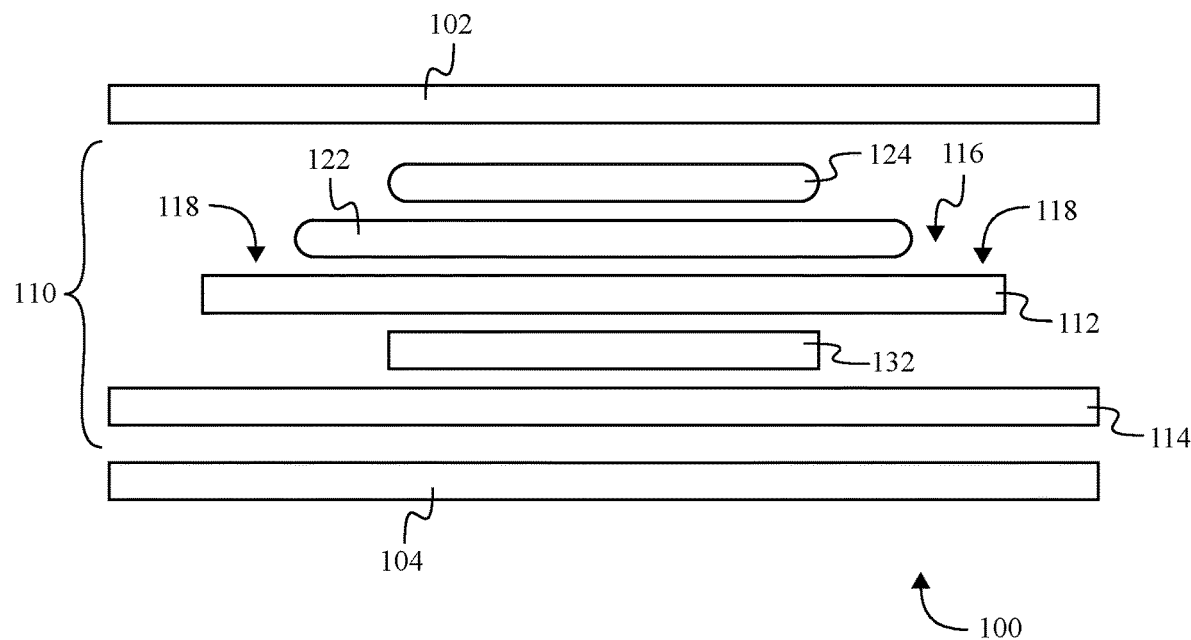
Figure 12:
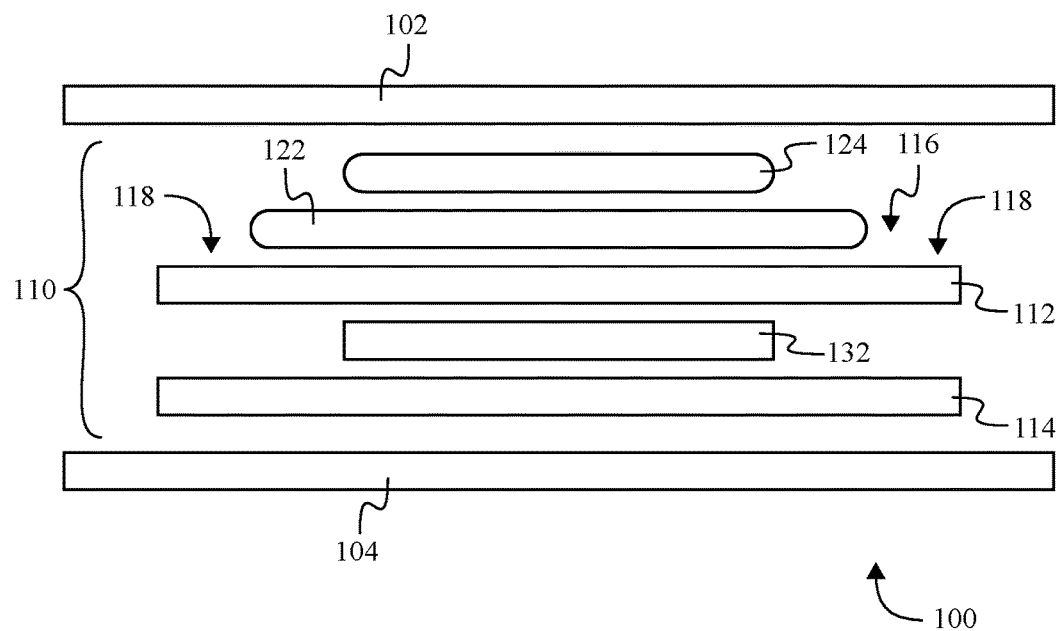

FIGS. 10 to 12 illustrate example embodiments of insert 110 comprising only two absorbent layers 122 and 124 (i.e. absorbent layer 126 is absent), and a third liquid barrier layer 132 disposed between liquid barrier layers 112 and 114. In FIG. 10, liquid barrier layers 112 and 114 have the same size and extend to an edge or perimeter of layers 102 and 104. In FIG. 11, liquid barrier layer 112 is smaller (at least across a width of the insert middle section) than liquid barrier layer 114, with liquid barrier layer 114 extending to an edge or perimeter of layers 102 and 104, and liquid barrier layer 112 spaced or set back from the edge or perimeter of layers 102 and 104. In FIG. 12, liquid barrier layers 112 and 114 have the same size and are spaced or set back from the edge or perimeter of layers 102 and 104.

Figure 13:
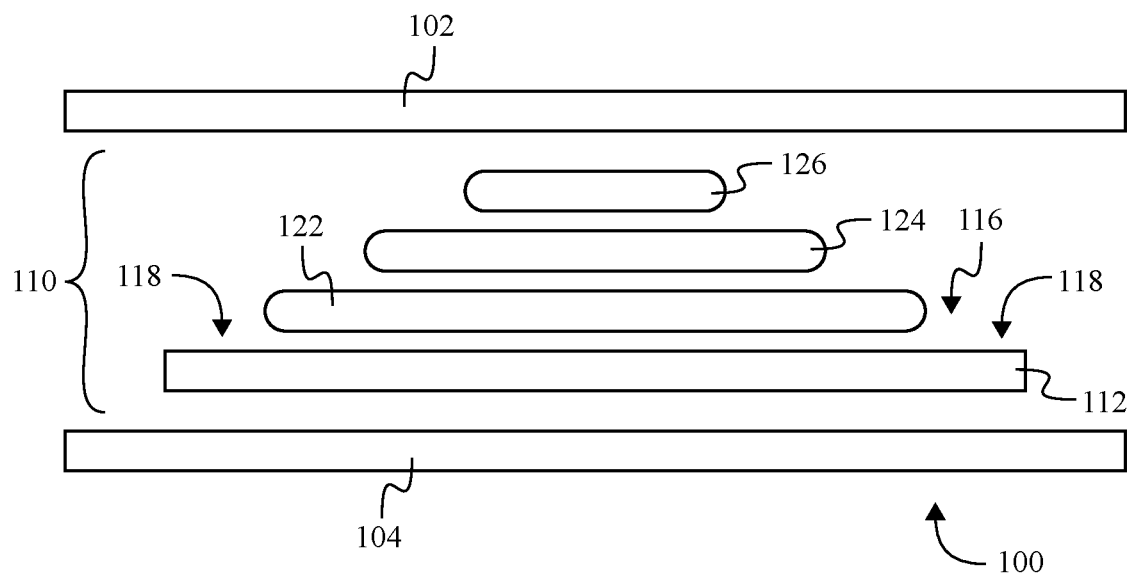
Figure 14:
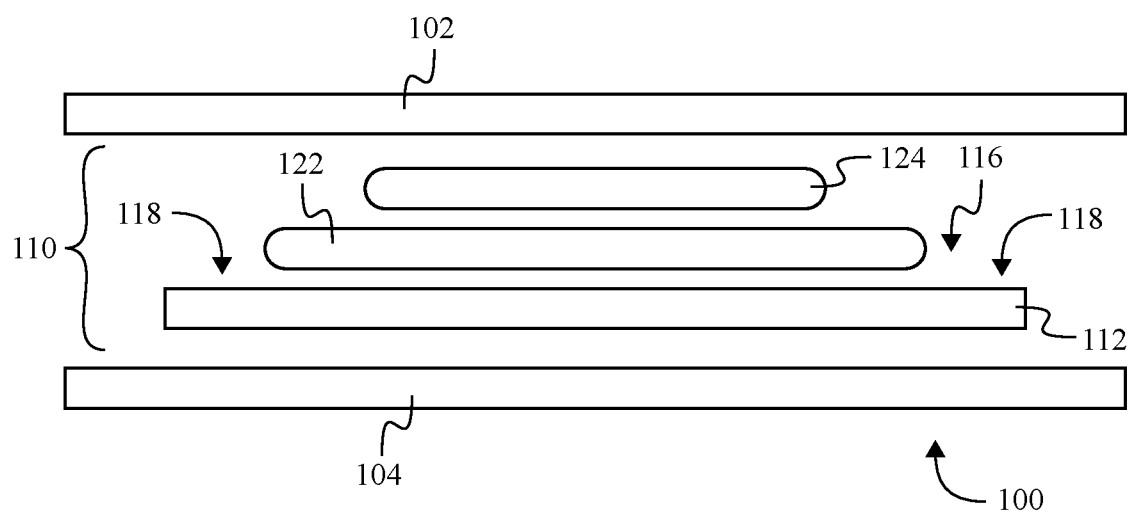
Figure 15:
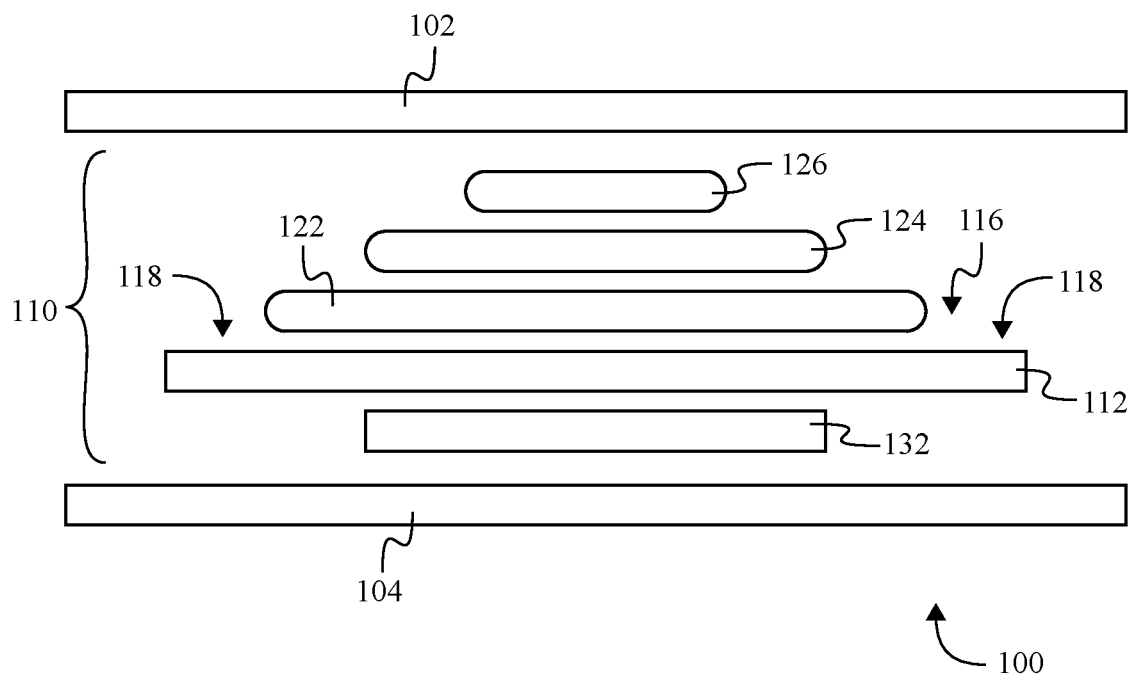
Figure 16:
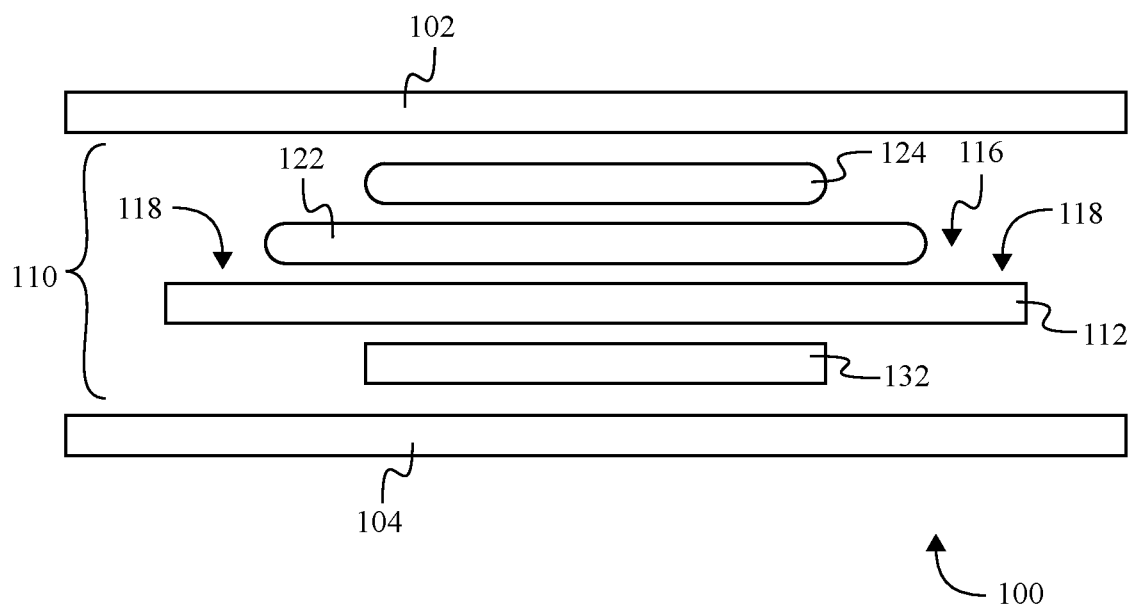

FIGS. 13 to 16 illustrate example embodiments of insert 110 comprising only one liquid barrier layer 112 (i.e. liquid barrier layer 114 is absent). Liquid barrier layer 112 is smaller (i.e. narrower in width) than layers 102 and 104, spaced or set back from an edge or perimeter of layers 102 and 104. In FIG. 13, insert 110 comprises three absorbent layers 122, 124, and 126. In FIG. 14, insert 110 comprises only two absorbent layers 122 and 124 (i.e. absorbent layer 126 is absent). In FIGS. 15 and 16, insert 110 comprises a second liquid barrier layer 132 having a smaller size (at least across a width of the insert middle section) than liquid barrier layer 112, and being disposed between liquid barrier layer 112 and outer layer 104. In FIG. 15, insert 110 comprises three absorbent layers 122, 124, and 126. In FIG. 16, insert 110 comprises only two absorbent layers 122 and 124 (i.e. absorbent layer 126 is absent).

Figure 17:
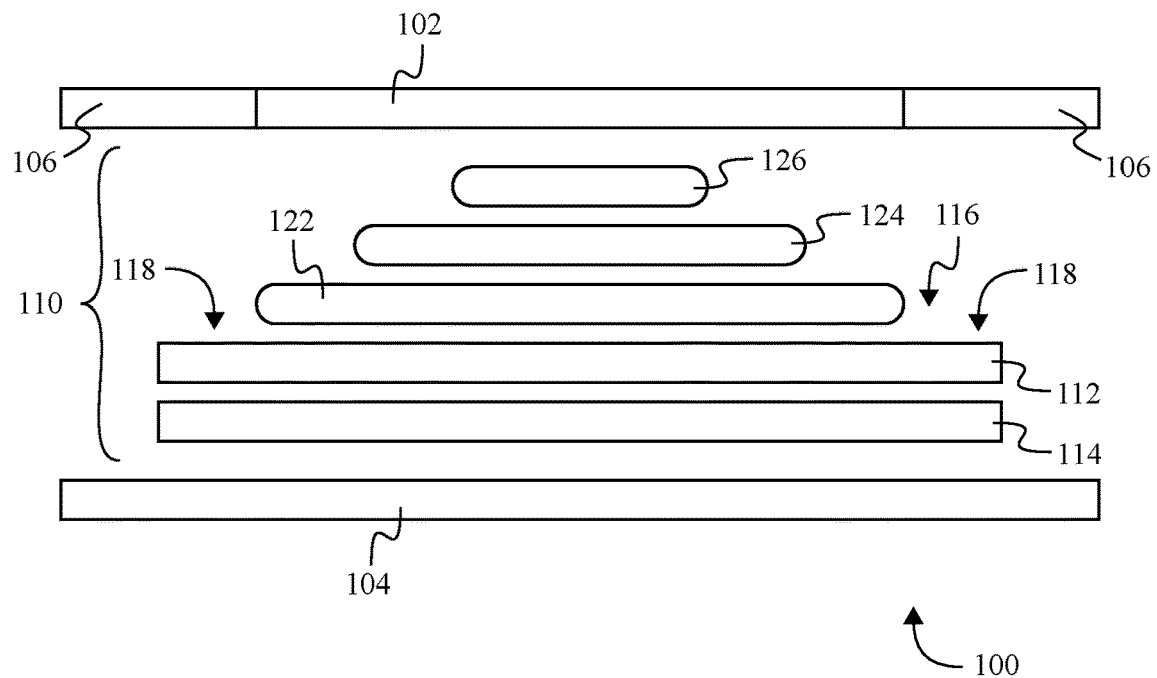

FIG. 17 illustrates an example embodiment of garment 100 further comprising hydrophobic material 106 attached to or lining at least a portion of a peripheral region of inner layer 102, such as the portion of inner layer 102 overlapping or opposite to the portion of peripheral region 118 that is left uncovered by absorbent layer 122. Hydrophobic material 106 may be provided in the form of strips or patches, which may have the same or a similar thickness to that of inner layer 102. Hydrophobic material 106 may also be liquid-impermeable. This configuration is intended to reduce or prevent transfer of body fluid absorbed or accumulated in a central region of inner layer 102 to an edge or perimeter of inner layer 102. It is to be understood that other configurations of the insert shown in FIG. 17 are possible, such as the configurations described above. For instance, in another example, third absorbent layer 126 may be excluded. In other examples, liquid barrier layers 112 and 114 extend to an edge or perimeter of inner layer 102 and outer layer 104. More generally, hydrophobic material 106 may be included in any of the other variations described above.

As explained above, each liquid barrier layer may comprise a polymer film layer and a fabric layer disposed adjacent to polymer film layer. FIGS. 39 to 42 illustrate some example orientations into which the liquid barrier layers may be arranged.

Figure 39:
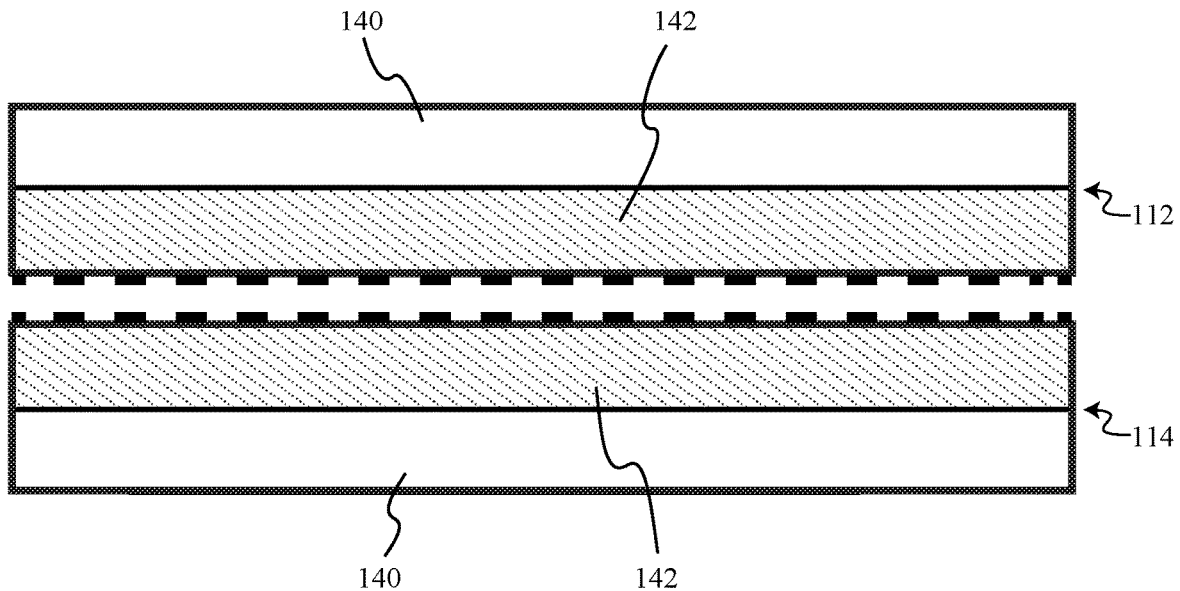
FIG. 39 is a cross-sectional view of an example arrangement of two liquid barrier layers of an insert for managing body fluid.

FIG. 39 illustrates an example arrangement of two liquid barrier layers, as may be found in the example inserts illustrated in FIGS. 1 to 6 and 17. Liquid barrier layer 112 is oriented such that its polymer film layer (e.g. polyurethane membrane) 140 is wearer-facing and its fabric layer (e.g. polyester knit fabric) 142 is out-facing. Liquid barrier layer 114 is oriented such that its polymer film layer 140 is out-facing and its fabric layer 142 is wearer-facing. That is, liquid barrier layers 112 and 114 are oriented such that their respective fabric layers 142 are opposite to or face each other. Opposite fabric layers 142 of liquid barrier layers 112 and 114 are typically arranged such that air is permitted to flow therebetween. Other examples may have the polymer film layers facing one another, or alternatively, the polymer film layer of one of the liquid barrier layers may face the fabric layer of the other of the liquid barrier layers.

Figure 40:
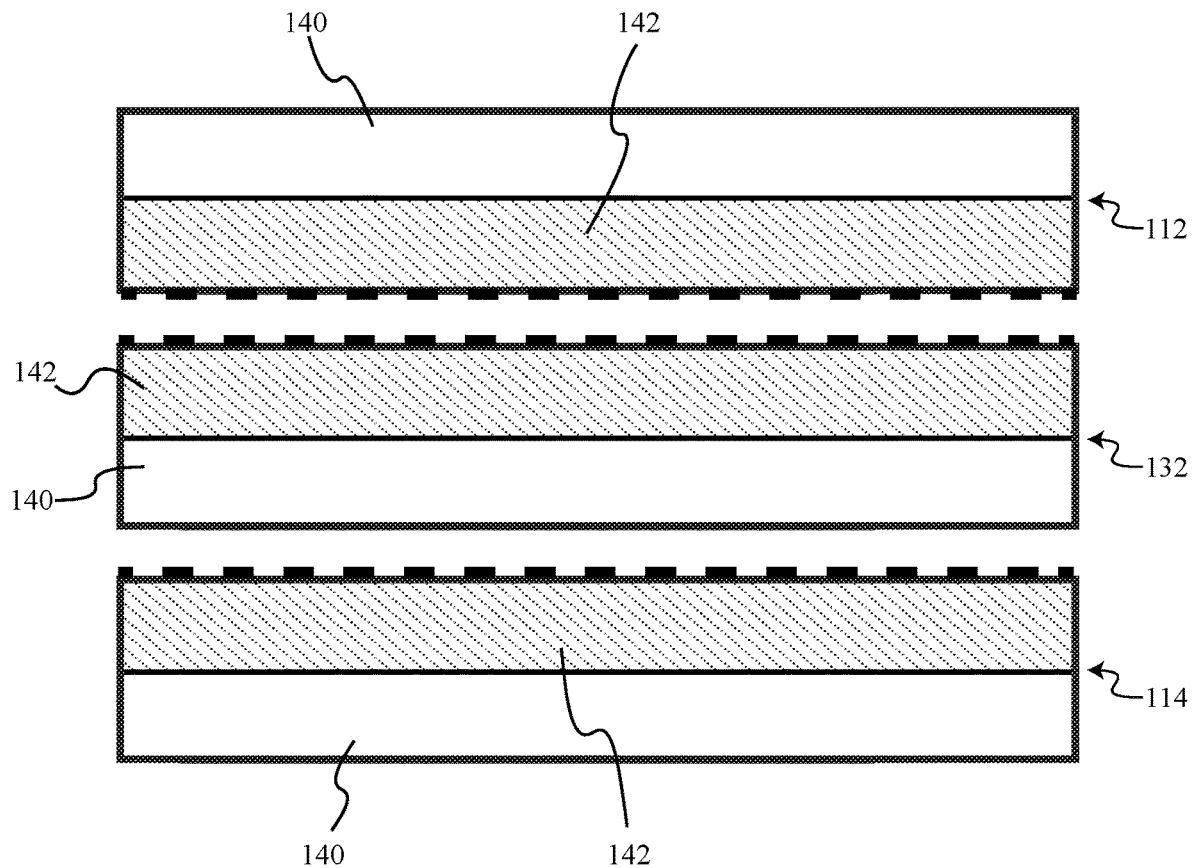
FIG. 40 is a cross-sectional view of an example arrangement of three liquid barrier layers of an insert for managing body fluid.

FIG. 40 illustrates an example arrangement of three liquid barrier layers, as may be found in the example inserts illustrated in FIGS. 7 to 12. Liquid barrier layer 112 is oriented such that its polymer film layer 140 is wearer-facing and its fabric layer 142 is out-facing. Liquid barrier layers 114 and 132 are oriented such that their respective polymer film layers 140 are out-facing and their respective fabric layers 142 are wearer-facing. That is, liquid barrier layers 112 and 132 are oriented such that their respective fabric layers 142 are opposite to or face each other.

Figure 41:
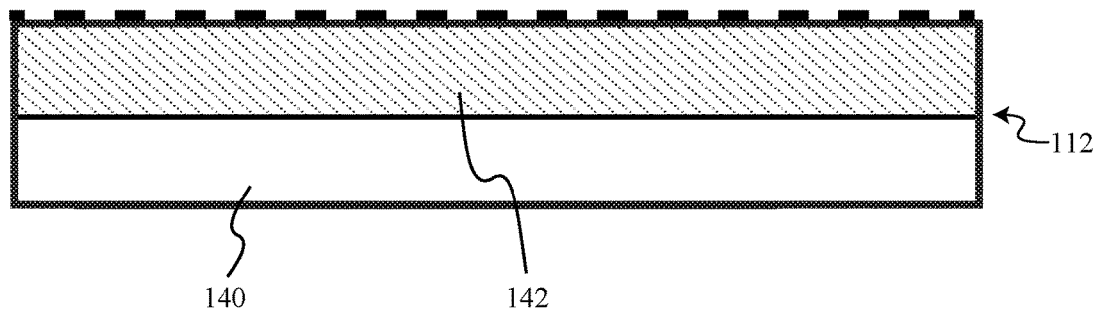
FIG. 41 is a cross-sectional view of an example arrangement of a single liquid barrier layer of an insert for managing body fluid.

FIG. 41 illustrates an example arrangement of one liquid barrier layer, as may be found in the example inserts illustrated in FIGS. 13 and 14. Liquid barrier layer 112 is oriented such that its polymer film layer 140 is out-facing and its fabric layer 142 is wearer-facing. That is, liquid barrier layer 112 is oriented such that fabric layer 142 is opposite to or faces first absorbent layer 122.

Figure 42:
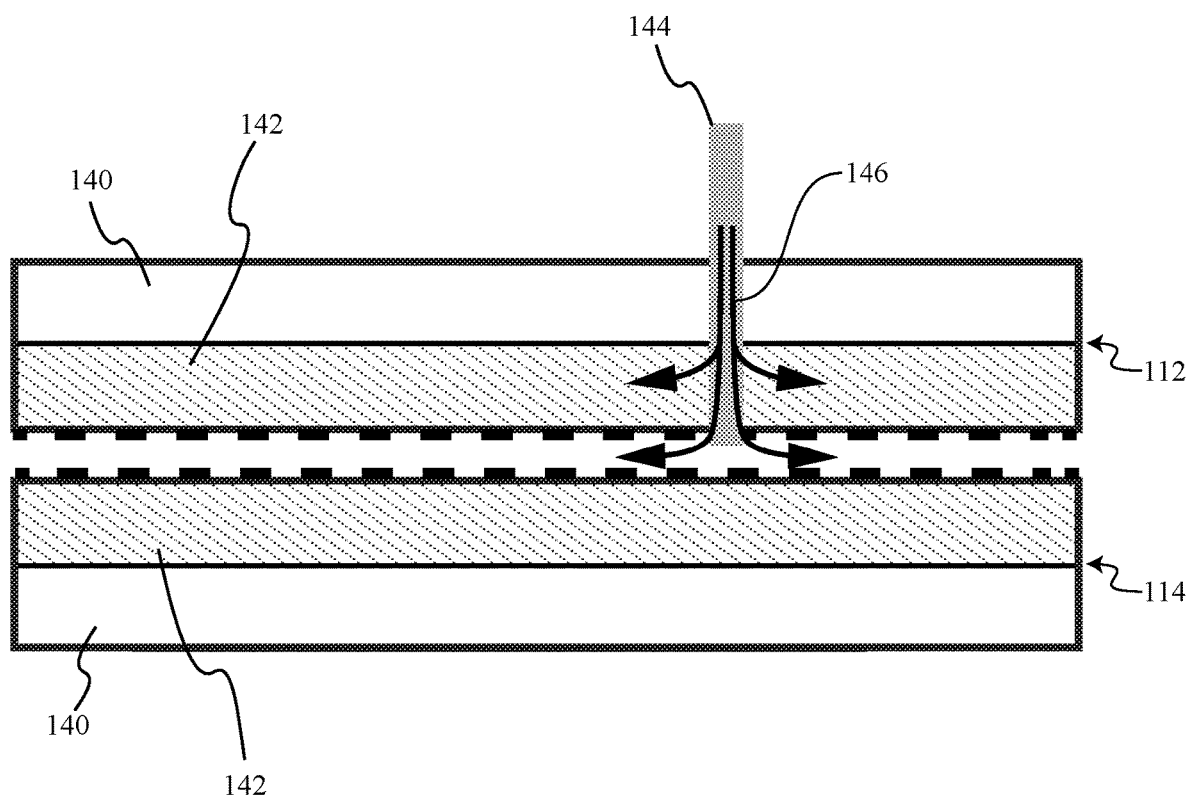
FIG. 42 is a cross-sectional view of an example arrangement of two liquid barrier layers of an insert for managing body fluid, showing a stitching thread location.

FIG. 42 illustrates an example arrangement of two liquid barrier layers, in which a stitching thread 144 penetrates first liquid barrier layer 112 as may be the case when, for example, liquid barrier layer 112 is stitched to an adjacent absorbent layer (not shown), as described above. Stitching thread 144 penetrates through the whole thickness of liquid barrier layer 112 to an interfacing region between liquid barrier layer 112 and liquid barrier layer 114, disposed adjacent to the out-facing side of liquid barrier layer 112. Stitching thread 144 however does not extend or penetrate liquid barrier layer 114. In this way, any fluid passing through liquid barrier layer 112 via stitching thread 144 may be trapped in and/or between the respective fabric layers 142 of liquid barrier layers 112 and 114, as indicated by fluid flow arrows 146. The airflow permitted between liquid barrier layers 112 and 114 facilitates drying of the trapped fluid.

The provision of two (or more) liquid barrier layers is independently advantageous, and therefore, such layer arrangements may also be implemented more broadly for leak prevention, in other inserts or garments, beyond the particular embodiments described herein (e.g. beyond use with absorbent layers as described herein). As described above, the liquid barrier layers may comprise a polymer film layer and a fabric layer. Arrangements whereby the fabric layers of the liquid barrier layers face one another provides especially improved leak prevention performance. Although, other orientations, whereby the polymer film layers face one another, or whereby the fabric layer of one of the liquid barrier layers faces the polymer film layer of the other liquid barrier layer, also provide improved performance over existing leak prevention arrangements.

To further facilitate management of body fluid the fabric layers of the liquid barrier layers may have their grains aligned to direct or encourage fluid flowing along or between liquid barrier layers. For example, in the case of insert configured for a crotch region, the grains may be oriented to direct or encourage liquid to travel in a forward or rear direction, as opposed to a lateral direction toward the leg openings. This is typically achieved by having the straight grain of the fabric travelling front to back, as opposed to side to side between leg openings An example of male or female underpants 200 is illustrated in FIG. 18, and an example insert 210 shaped to conform to a crotch region 202 of underpants 200 is illustrated in FIG. 19.

Insert 210 comprises a liquid barrier layer 212, a first absorbent layer 222, and a second absorbent layer 224. Absorbent layer 222 is disposed adjacent to a wearer-facing side of liquid barrier layer 212, while absorbent layer 224 is disposed adjacent to a wearer-facing side of absorbent layer 222. It will be appreciated that, in other examples, insert 210 may comprise other liquid barrier layers and/or absorbent layers, such as a third absorbent layer disposed adjacent to a wearer-facing side of absorbent layer 224. Variations may comprise, for example, any one of the layer configurations/edge profiles/inserts shown in FIGS. 1 to 17

Figure 18:
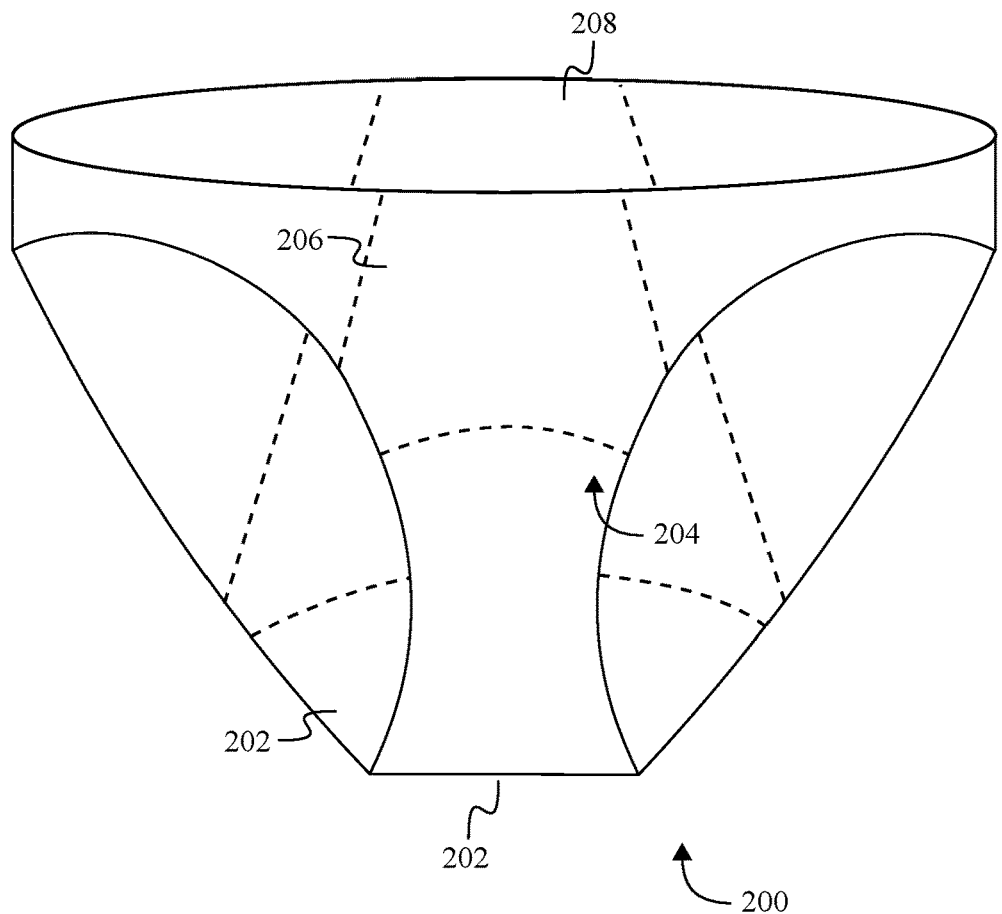
FIG. 18 is a front view of an example pair of male or female underpants.
Figure 19:
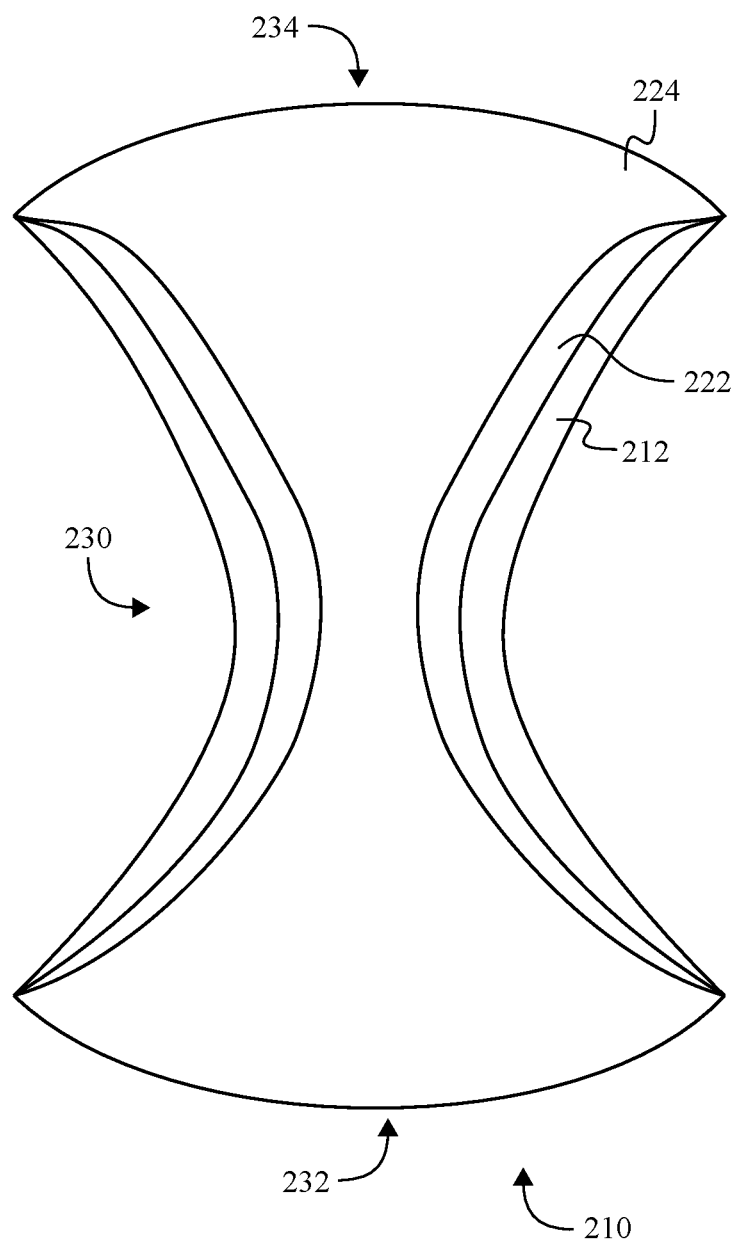
FIG. 19 is a top view of an example insert for managing body fluid shaped to conform to a crotch region of underpants.

Referring to FIGS. 18 and 19, the body of liquid barrier layer 212 comprises a middle section 230, a front section 232, and a rear section 234. Middle section 230 is configured to fit between the thighs of the wearer. Middle section 230 is defined between two concave-shaped sides of liquid barrier layer 212 configured to accommodate or fit around the inner thighs of the wearer. Front section 232 extends from middle section 230 towards a front side 204 of underpants 200. Rear section 234 extends from middle section 230 towards a rear side of underpants 200. Therefore, when underpants 200 are worn, front section 232 is configured to adjoin or be located proximate to a front region of the wearer's crotch, while rear region 234 is configured to adjoin or be located proximate to a rear region of the wearer's crotch.

In other examples, described below, the front section of insert 210 may be lengthened or extended to reach an inguinal region 206 of underpants 200 configured to adjoin or be located proximate to the wearer's inguinal region or groin. The rear section of the insert may also be lengthened or extended to reach a gluteal region 208 on the rear side of underpants 200 configured to adjoin or be located proximate to the wearer's buttock.

The shape of absorbent layers 222 and 224 resembles or conforms to the shape of liquid barrier layer 212. In other examples, the shape of the absorbent layers may differ to obtain different shapes and sizes of an uncovered or exposed portion of liquid barrier layer 212. For example, the size of the exposed portion of liquid barrier layer 212 in rear section 234 may be increased by reducing the size of absorbent layers 222 and 224 so that the wearer's sit bones do not lie directly on the absorbent layers when the wearer is in a seating position, reducing wearer discomfort. Additional absorbent layers may then be provided to compensate for any reduced absorption capacity of the smaller absorbent layers 222 and 224.

Figure 20:
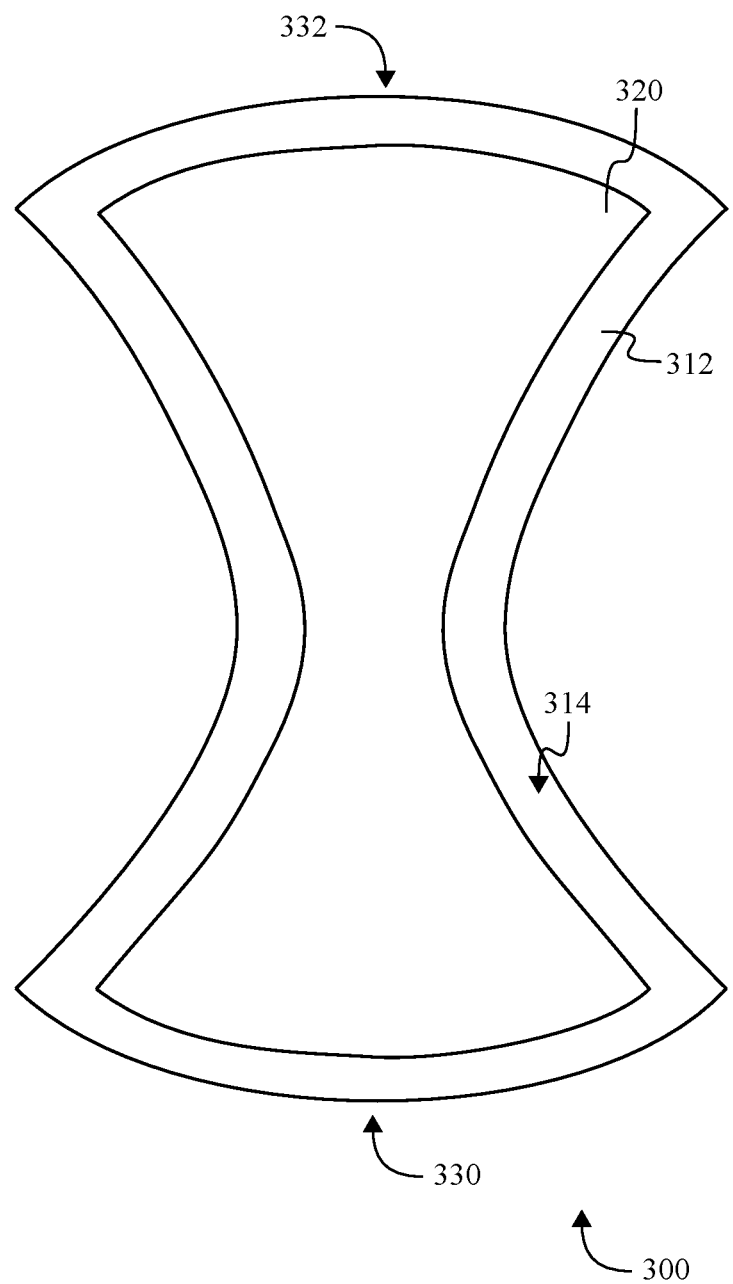
FIG. 20 is a top view of another example insert for managing body fluid shaped to conform to a crotch region of underpants.
Figure 21:
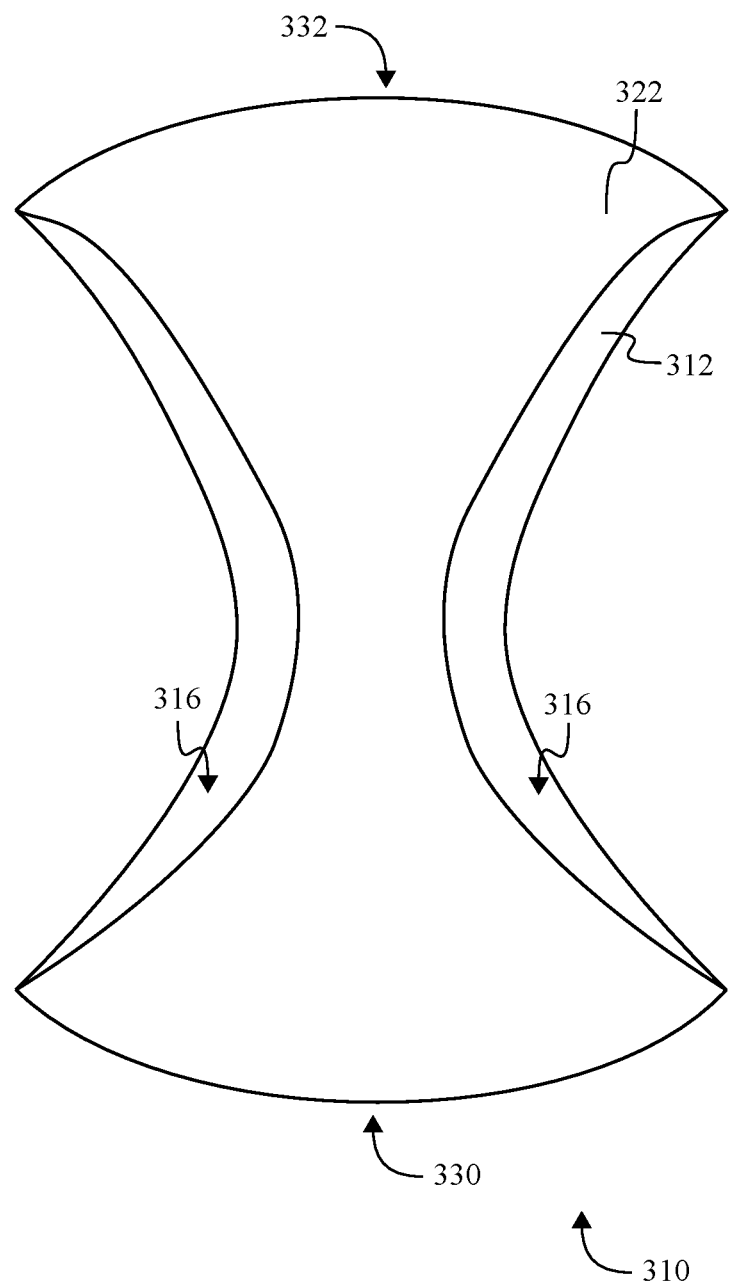
FIG. 21 is a top view of another example insert for managing body fluid shaped to conform to a crotch region of underpants.

FIGS. 20 and 21 illustrate example inserts 300 and 310, respectively, shaped to conform to a crotch region of male or female underpants, for insertion therein.

Each of inserts 300 and 310 comprises a liquid barrier layer 312. Inserts 300 and 310 comprise absorbent layers 320 and 322, respectively, disposed adjacent to a wearer-facing side of liquid barrier layer 312. In other examples, inserts 300 and 310 comprise other liquid barrier layers and/or absorbent layers, such as second and third absorbent layers disposed adjacent to a wearer-facing side of absorbent layer 320 and 322, respectively. Variations may comprise, for example, any one of the layer configurations shown in FIGS. 1 to 17.

In insert 300, the peripheral region 314 of the wearer-facing side of liquid barrier layer 312 that is left uncovered by absorbent layer 320 extends around the whole perimeter of the wearer-facing side. In insert 310, the peripheral region 316 of the wearer-facing side of liquid barrier layer 312 that is left uncovered by absorbent layer 322 extends only over a portion of the perimeter of the wearer-facing side, specifically the perimeter neighbouring the concave sides of liquid barrier layer 312. Therefore, absorbent layer 322 of insert covers front and rear sections of insert 310, extending to frontmost edge 330 and rearmost edge 332.

Figure 22:
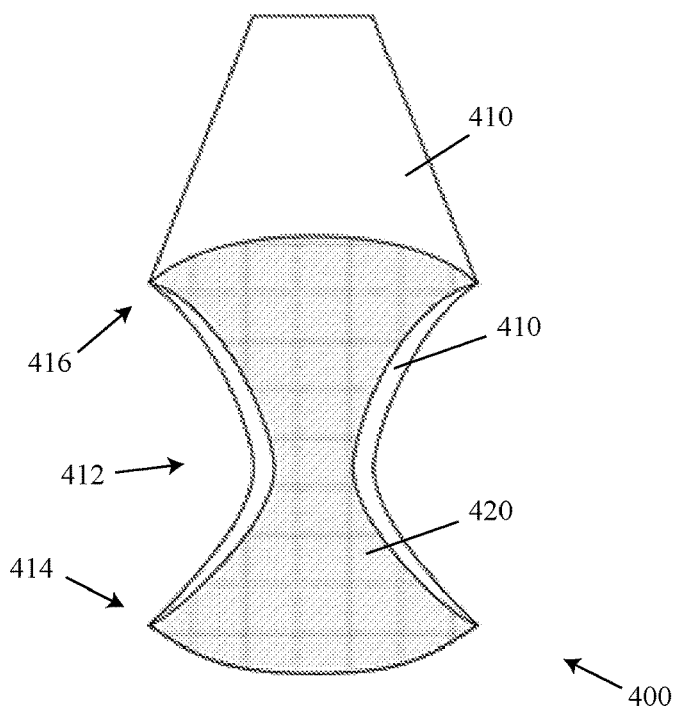
FIG. 22 is a top view of another example insert for managing body fluid shaped to conform to a crotch region of underpants, the insert having an extended rear section.

FIG. 22 illustrates another example insert 400 shaped to conform to a crotch region of male or female underpants, for insertion therein. Insert 400 comprises a liquid barrier layer 410 and an absorbent layer 420. The body of liquid barrier layer 410 comprises a middle section 412, a front section 414, and a rear section 416, as described above with reference to FIG. 19. Front section 414 is arc-shaped, while rear section 416 is a trapezoid-shaped flap that is lengthened relative to rear section 234 in FIG. 19. Absorbent layer 420 extends to a frontmost edge of front section 414, so that the uncovered peripheral region of the wearer-facing side of liquid barrier layer 410 comprises lateral edges of middle section 412 and the trapezoidal flap in rear section 416.

Figure 23:
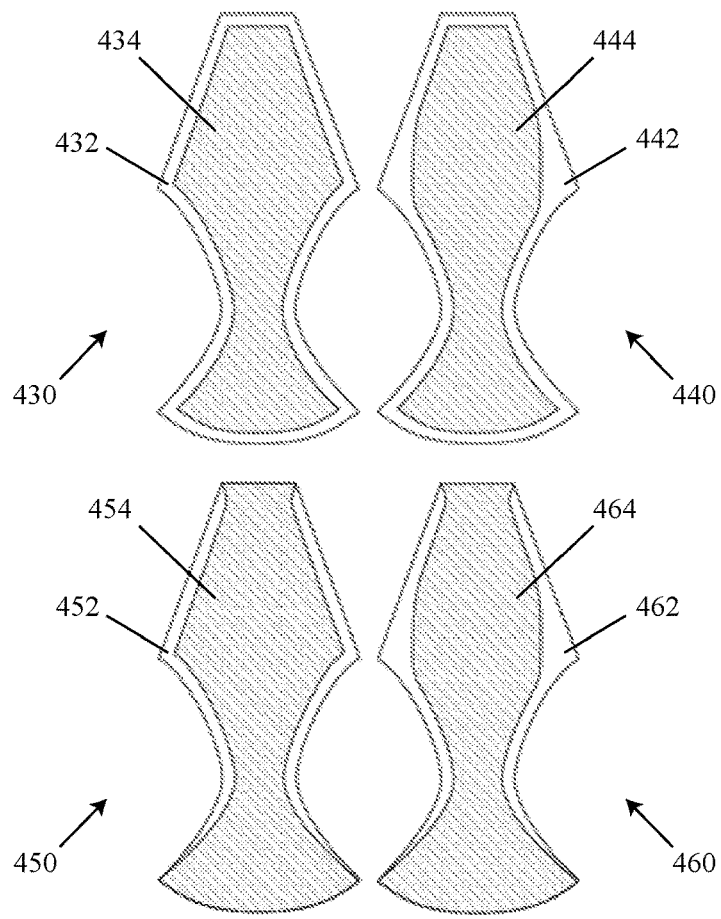
FIG. 23 is a top view of different configurations of the insert of FIG. 22.

FIG. 23 illustrates different example insert configurations having the same overall shape illustrated in FIG. 22. In configuration 430, the peripheral region of the wearer-facing side of liquid barrier layer 432 that is uncovered by absorbent layer 434 extends along the whole perimeter of liquid barrier layer 432 and has the same width throughout. In configuration 440, the peripheral region of the wearer-facing side of liquid barrier layer 442 uncovered by absorbent layer 444 extends along the whole perimeter of liquid barrier layer 442 and its width increases at and near the junction between the middle and rear sections of liquid barrier layer 442. In configuration 450, the peripheral region of the wearer-facing side of liquid barrier layer 452 uncovered by absorbent layer 454 extends along a portion of the perimeter of liquid barrier layer 452, comprising the lateral edges of liquid barrier layer 452, but not the frontmost and rearmost edges. In configuration 460, the peripheral region of the wearer-facing side of liquid barrier layer 462 uncovered by absorbent layer 464 extends along a portion of the perimeter of liquid barrier layer 462, comprising the lateral edges of liquid barrier layer 462, but not the frontmost and rearmost edges, and the uncovered peripheral region widens at and near the junction between the middle and rear sections of liquid barrier layer 462.

Figure 24:
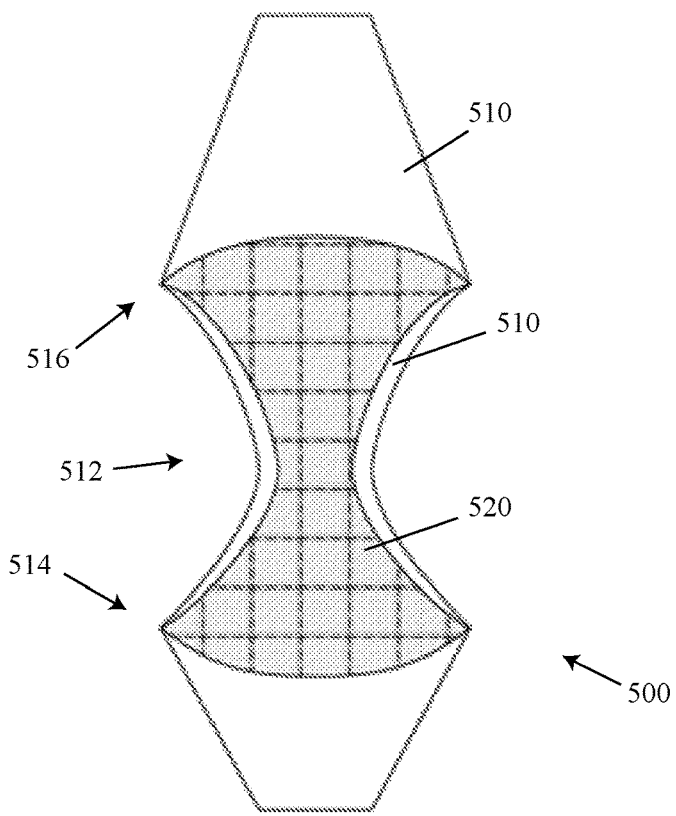
FIG. 24 is a top view of another example insert for managing body fluid shaped to conform to a crotch region of underpants, the insert having extended front and rear sections.

FIG. 24 illustrates another example insert 500 shaped to conform to a crotch region of male or female underpants, for insertion therein. Insert 500 comprises a liquid barrier layer 510 and an absorbent layer 520. The body of liquid barrier layer 510 comprises a middle section 512, a front section 514, and a rear section 516, as described above with reference to FIG. 19. Front section 514 and rear section 516 are trapezoid-shaped, and each comprises a flap that is lengthened relative to front section 232 and rear section 234, respectively, in FIG. 19. Absorbent layer 520 covers most of middle section 512, so that the uncovered peripheral region of the wearer-facing side of liquid barrier layer 510 comprises lateral edges of middle section 512 and the trapezoidal flaps in front section 514 and in rear section 516.

Figure 25:
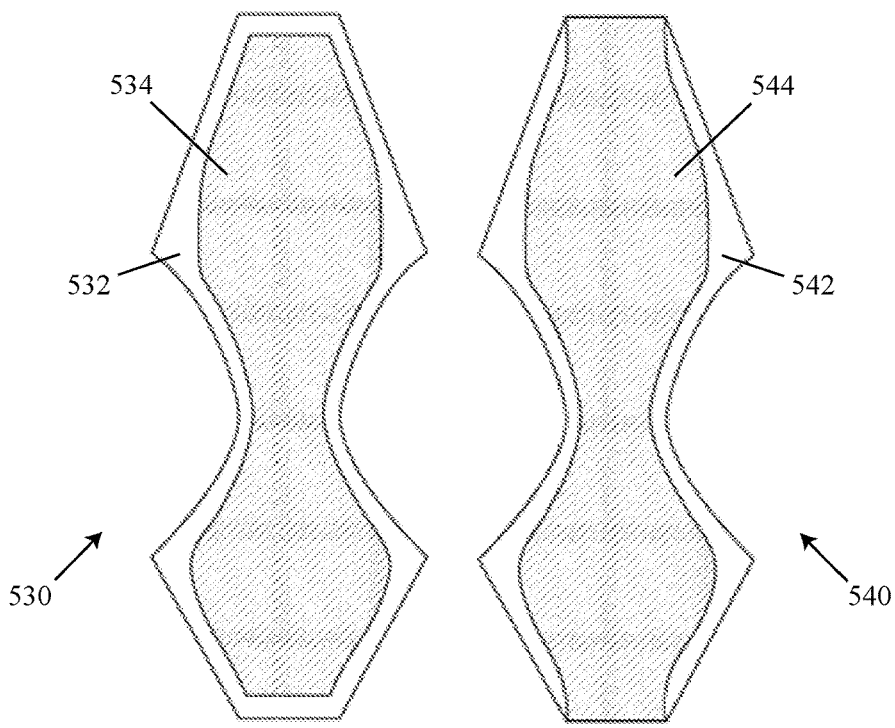
FIG. 25 is a top view of different configurations of the insert of FIG. 24.

FIG. 25 illustrates different example insert configurations having the same overall shape illustrated in FIG. 24. In configuration 530, the peripheral region of the wearer-facing side of liquid barrier layer 532 uncovered by absorbent layer 534 extends along the whole perimeter of liquid barrier layer 532. In configuration 540, the peripheral region of the wearer-facing side of liquid barrier layer 542 uncovered by absorbent layer 544 extends along a portion of the perimeter of liquid barrier layer 542, comprising the lateral edges, but not the frontmost and rearmost edges, of liquid barrier layer 542.

It will be appreciated that the example embodiments illustrated in FIGS. 20 to 25, which have been represented with a single liquid barrier layer and a single absorbent layer, may alternatively have additional liquid barrier layers and/or additional absorbent layers. It will also be appreciated that whilst suitable for conventional shaped underpants that do not have leg portions, that may also be implanted in boxer-brief type underpants that have a small leg portion.

Having the absorbent layer(s) extend to the frontmost and/or rearmost edges of the first liquid barrier layer (e.g. like in examples 310, 450, 460, and 540) provides a more durable insert/garment, as this permits the layers to be more robustly secured together. These forms may be used, in the case of a menstruation-fluid-capturing undergarment, for example, when the wearer is being particularly active, such as, for example, when going to the gym or hiking, etc.

Figure 26:
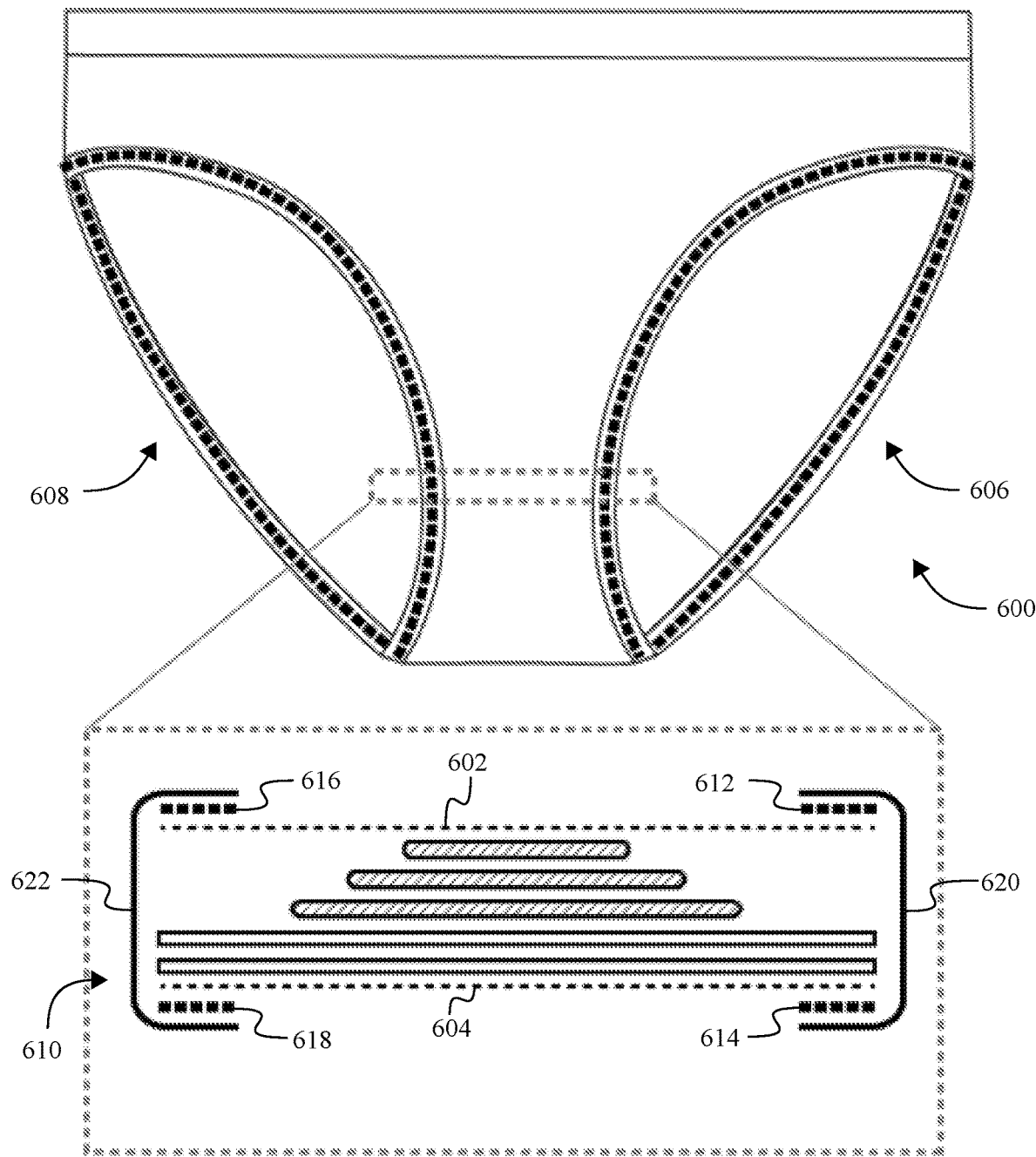
FIG. 26 is a front view of another example pair of male or female underpants showing a cross-sectional view of an example insert for managing body fluid inserted in the underpants.

FIG. 26 illustrates an example pair of underpants 600 comprising an insert 610 for managing body fluid discharged (e.g. menstruation fluid, urine) by a wearer of underpants 600.

Underpants 600 comprise an inner fabric layer 602 and an outer fabric layer 604. Each of fabric layers 602 and 604 comprises both an opening 606 for the wearer's left leg and an opening 608 for the wearer's right leg. A first strip 612 of liquid-impermeable, elastic or stretch fabric lines left leg opening 606 in inner fabric layer 602. A second strip 614 of liquid-impermeable, elastic or stretch fabric lines left leg opening 606 in outer fabric layer 604. A third strip 616 of liquid-impermeable, elastic or stretch fabric lines the right leg opening 608 in inner fabric layer 602. A fourth strip 618 of liquid-impermeable, elastic or stretch fabric lines right leg opening 608 in outer fabric layer 604. Strips 612, 614, 616, and 618 are located on exterior surfaces of fabric layers 602 and 604. In other examples, the strips may alternatively or additionally be located on interior surfaces of the fabric layers.

A first band 620 of elastic fabric skirts or borders the edges of left leg openings 606 in both fabric layers 602 and 604. Likewise, a second band 622 of elastic fabric skirts or borders the edges of right leg openings 608 in both fabric layers 602 and 604. Band 620 overlaps strips 612 and 614, while band 622 overlaps strips 616 and 618. An interior surface (i.e. a fabric-facing surface) of bands 620 and 622 may be laminated with a polyurethane liquid-impermeable membrane, such as thermoplastic polyurethane (TPU) elastic rubber, to further deter seepage of body fluid into the fabric of underpants 600. The configuration of underpants 600 therefore prevents or reduces leakage of body fluid through leg openings 606 and 608.

Figure 27:
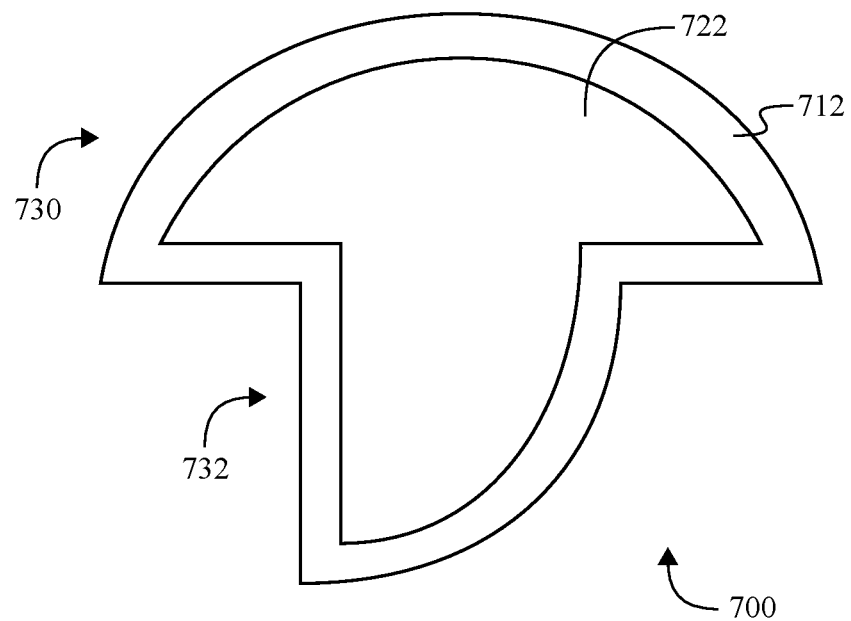
FIGS. 27 to 32 are top views of example inserts for managing body fluid shaped to conform to an armpit region of an upper body undergarment.
Figure 28:
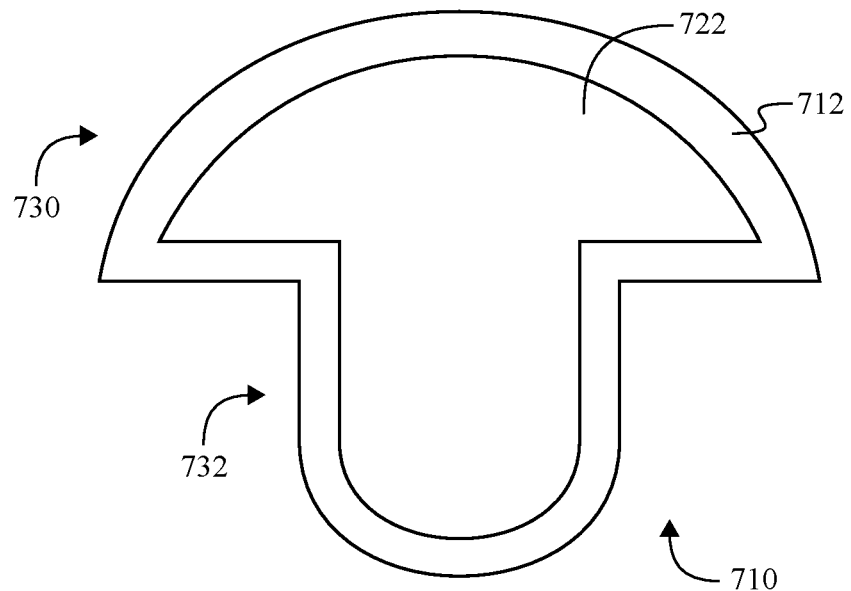

FIGS. 27 and 28 illustrates example inserts 700 and 710, respectively, shaped to conform to an armpit or underarm region of an upper body undergarment, such as a singlet, half singlet, or a shirt.

Each of inserts 700 and 710 comprises a liquid barrier layer 712 and an absorbent layer 722 disposed adjacent to a wearer-facing side of liquid barrier layer 712. The body of liquid barrier layer 712 comprises a top section 730 and a body section 732. Top section 730 is configured to adjoin or be located proximate to the wearer's upper armpit. Top section 730 includes a curved side and a straight side joining the two endpoints of the curved side, giving top section 730 a semicircular or arched shape. Body section 732 is configured to adjoin or be located proximate to the wearer's lower armpit. Body section 732 projects from the straight side of top section 730 in an opposite direction relative to the curved side of top section 730. body section 732 is fin-shaped in insert 700 and tongue-shaped in insert 710.

FIGS. 29 to 32 illustrate other example inserts shaped to conform to an armpit or underarm region of an upper body undergarment.

Figure 29:
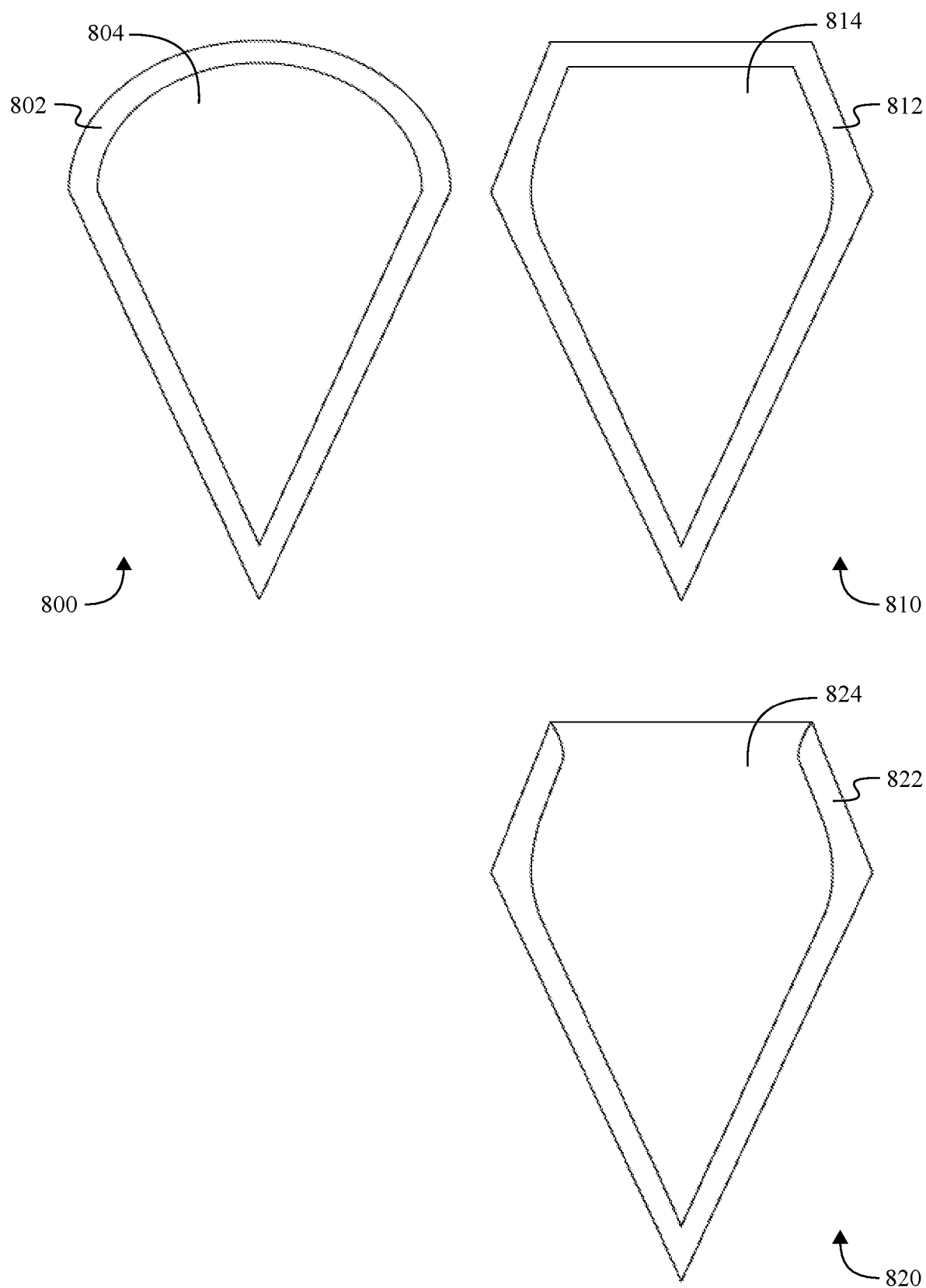

FIG. 29 shows insert configurations having pointed or triangular body sections. Configuration 800 has a rounded top section, and is configured for insertion in long-sleeved undergarments. Configurations 810 and 820 have trapezoid-shaped top sections, and are configured for insertion in short-sleeved undergarments. In configurations 800 and 810, the peripheral regions of the wearer-facing sides of liquid barrier layers 802 and 812 uncovered by absorbent layers 804 and 814, respectively, extend along the whole perimeters of liquid barrier layers 802 and 812, respectively. In configuration 820, the peripheral region of the wearer-facing side of liquid barrier layer 822 uncovered by absorbent layer 824 extends along a portion of the perimeter of liquid barrier layer 822 excluding the uppermost side of the top section.

Figure 30:
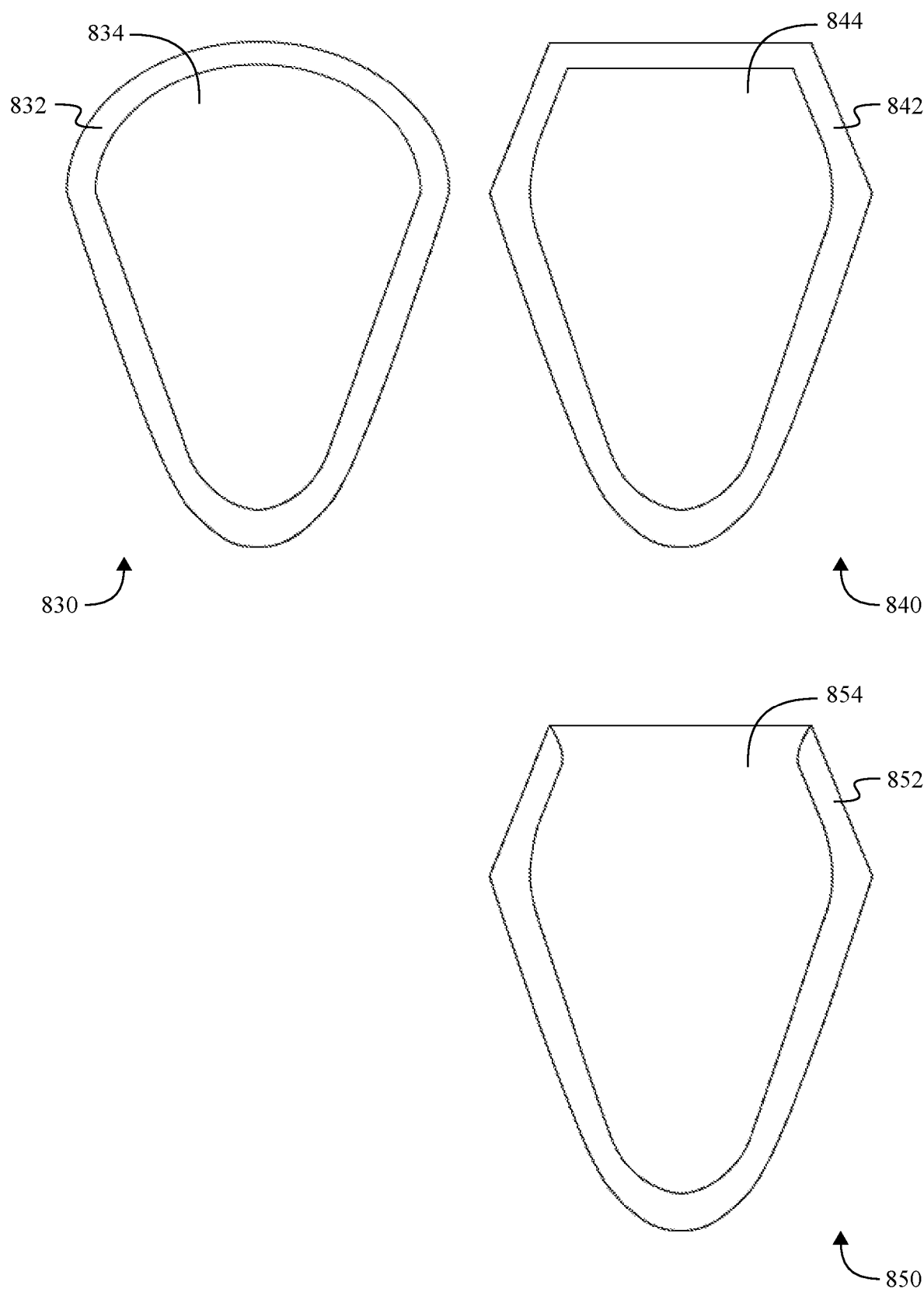

FIG. 30 shows insert configurations having rounded or parabolic body sections. Configuration 830 has a rounded top section, and is configured for insertion in long-sleeved undergarments. Configurations 840 and 850 have trapezoid-shaped top sections, and are configured for insertion in short-sleeved undergarments. In configurations 830 and 840, the peripheral regions of the wearer-facing sides of liquid barrier layers 832 and 842 uncovered by absorbent layers 834 and 844, respectively, extend along the whole perimeters of liquid barrier layers 832 and 842, respectively. In configuration 850, the peripheral region of the wearer-facing side of liquid barrier layer 852 uncovered by absorbent layer 854 extends along a portion of the perimeter of liquid barrier layer 852 excluding the uppermost side of the top section.

Figure 31:
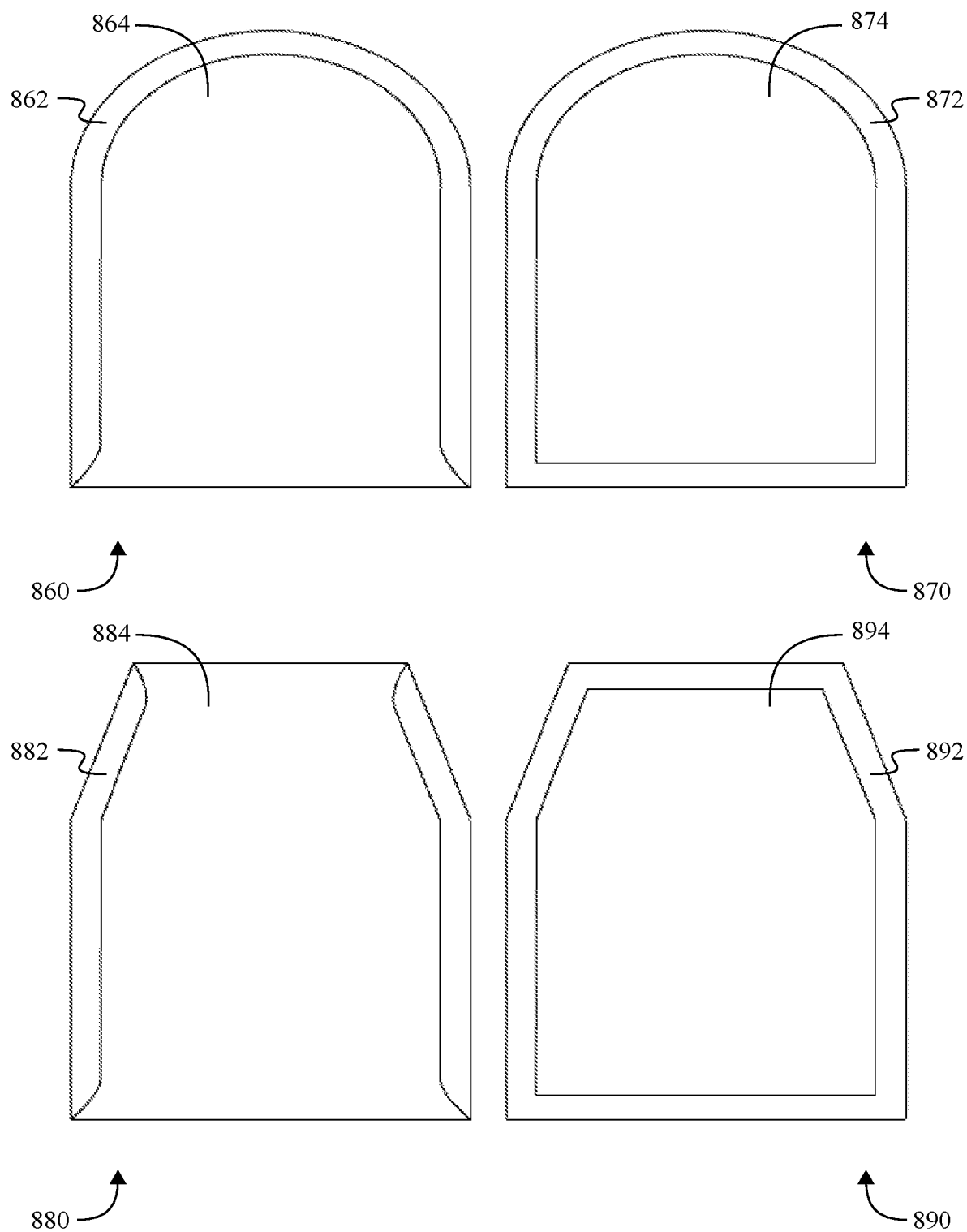

FIG. 31 shows insert configurations having square or rectangular body sections. Configurations 860 and 870 have rounded top sections, and are configured for insertion in long-sleeved undergarments. Configurations 880 and 890 have trapezoid-shaped top sections, and are configured for insertion in short-sleeved undergarments. In configuration 860, the peripheral region of the wearer-facing side of liquid barrier layer 862 uncovered by absorbent layer 864 extends along a portion of the perimeter of liquid barrier layer 862 excluding the lowermost side in the body section. In configurations 870 and 890, the peripheral regions of the wearer-facing sides of liquid barrier layers 872 and 892 uncovered by absorbent layers 874 and 894, respectively, extend along the whole perimeters of liquid barrier layers 872 and 892, respectively. In configuration 880, the peripheral region of the wearer-facing side of liquid barrier layer 882 uncovered by absorbent layer 884 extends along a portion of the perimeter of liquid barrier layer 882 excluding the lowermost side of the body section and the uppermost side of the top section.

Figure 32:
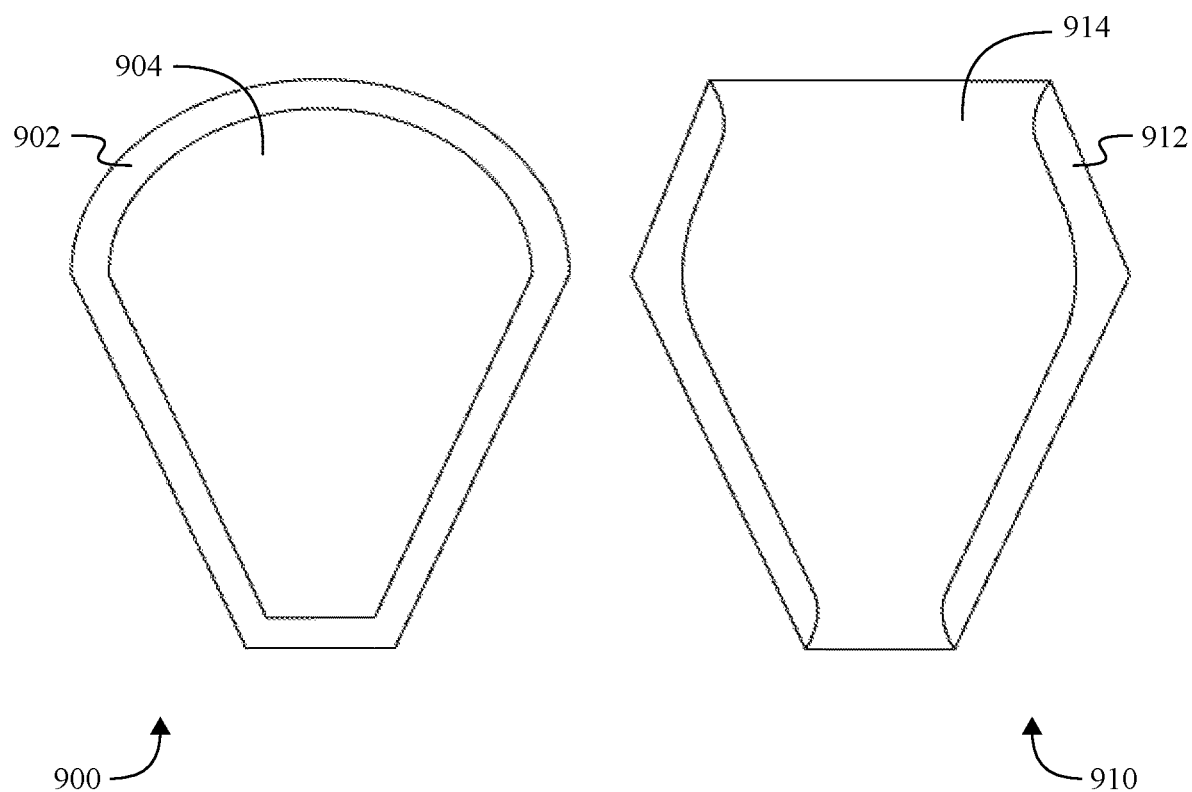

FIG. 32 shows insert configurations having trapezoidal or trapezoid-shaped body sections. Configuration 900 has a rounded top section, and is configured for insertion in long-sleeved undergarments. Configuration 910 has a trapezoid-shaped top section, and is configured for insertion in short-sleeved undergarments. In configuration 900, the peripheral region of the wearer-facing side of liquid barrier layer 902 uncovered by absorbent layer 904 extends along the whole perimeter of liquid barrier layer 902. In configuration 910, the peripheral region of the wearer-facing side of liquid barrier layer 912 uncovered by absorbent layer 914 extends along a portion of the perimeter of liquid barrier layer 912 excluding the lowermost side of the body section and the uppermost side of the top section.

It will be appreciated that the example embodiments illustrated in FIGS. 27 to 32, which have been represented with a single liquid barrier layer and a single absorbent layer, may alternatively have additional liquid barrier layers and/or additional absorbent layers.

Figure 33:
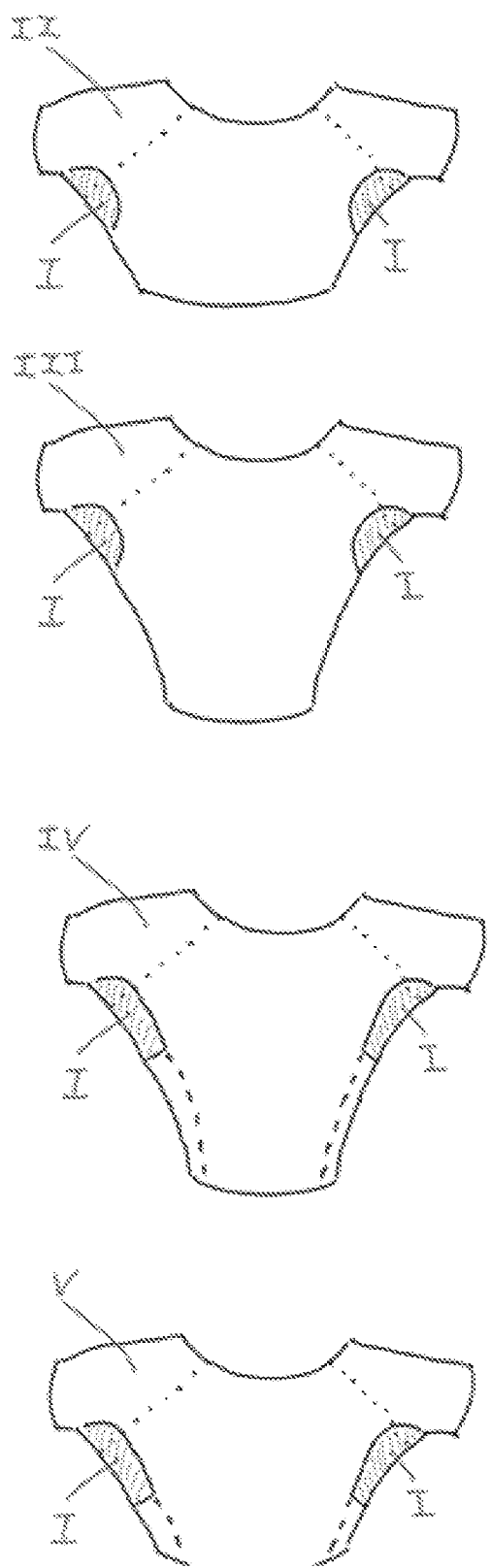
FIG. 33 is a front view of example upper body undergarments suitable for use with the inserts of FIGS. 27 to 32.

Example upper body undergarments are illustrated in FIG. 33, showing the armpit region near to arm holes, where a sleeve is joined with the vest or core, in which an insert for managing body fluid discharged by a wearer of the undergarment, such as one of the example inserts illustrated in FIGS. 27 to 32, may be inserted.

Figure 34:
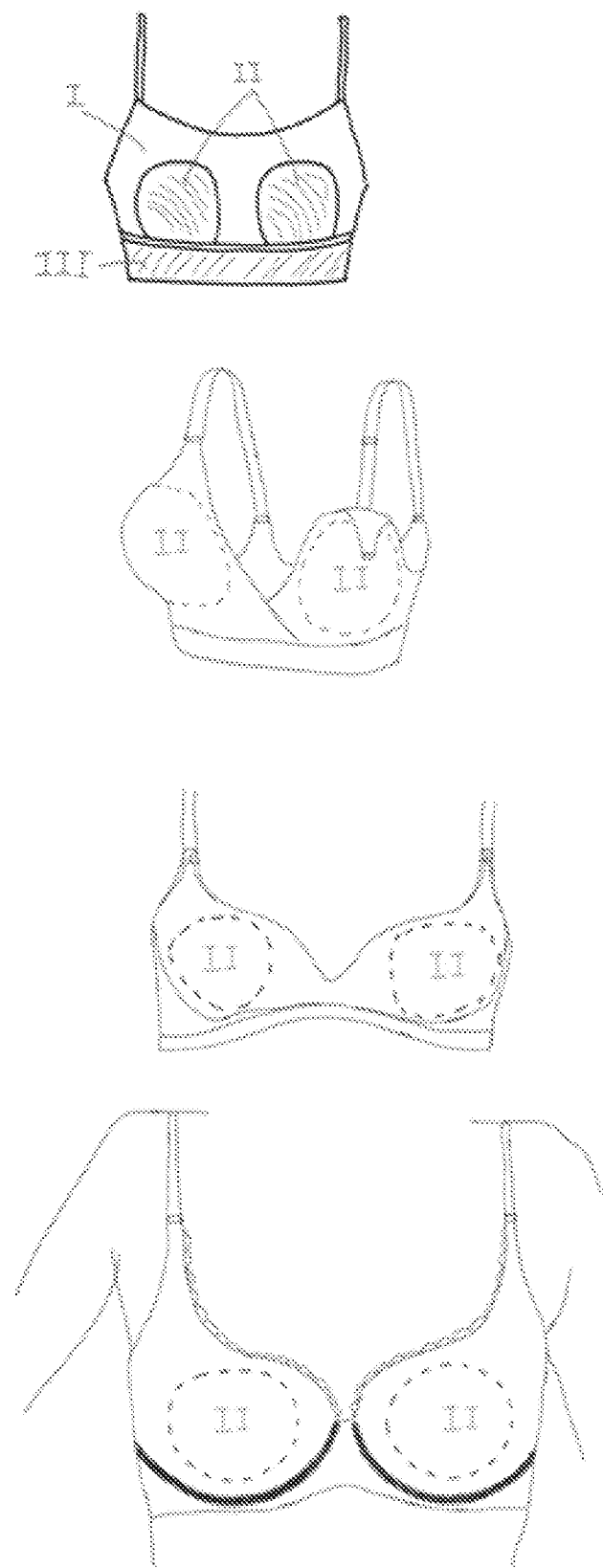
FIG. 34 shows example brassieres into which an insert for managing body fluid may be inserted.

FIG. 34 illustrates example brassieres into which may be inserted an insert for managing body fluid discharged by a wearer of the brassieres. Therefore, in some examples, the insert is shaped to conform to a cup of a brassiere, so as to cover the nipple area or the inframammary fold, including lateral and lower portions of a breast.

Figure 35:
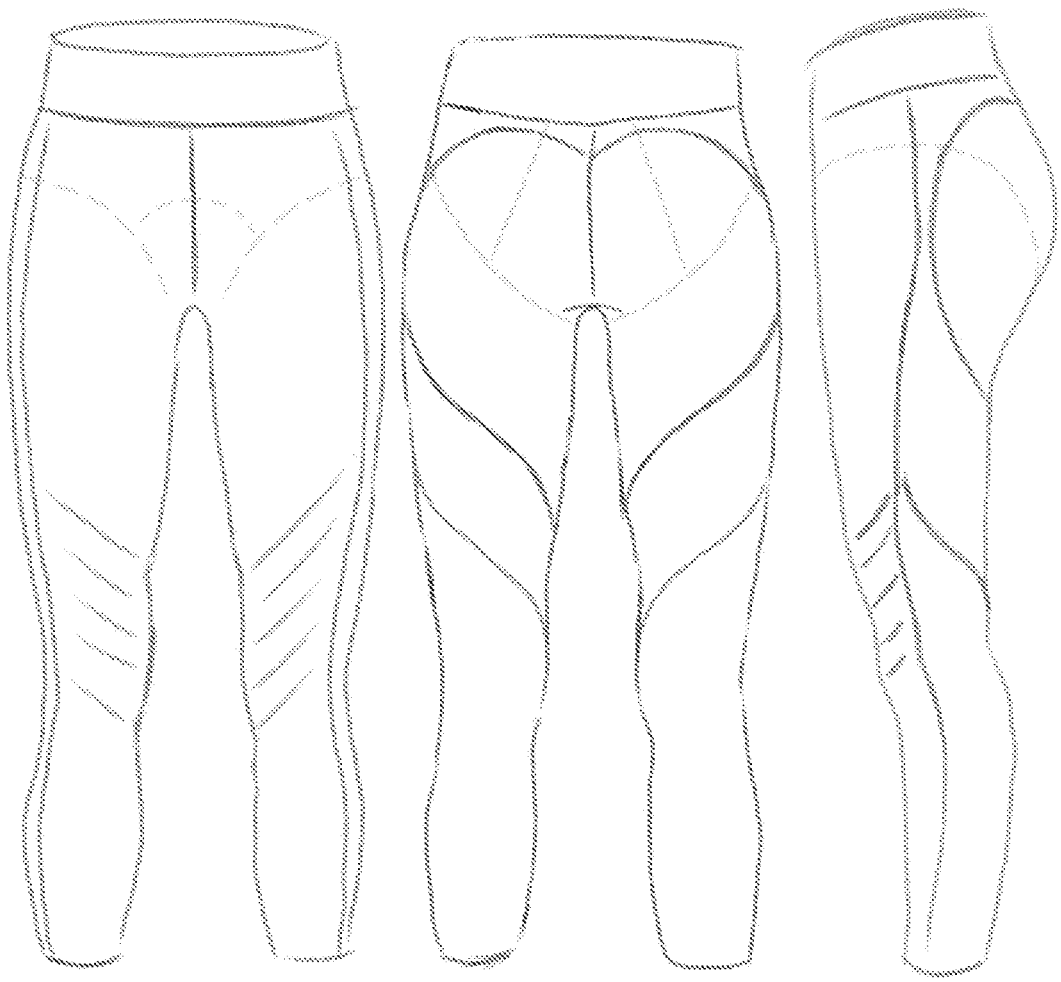
FIG. 35 shows front, rear, and side views of example pants into which an insert for managing body fluid may be inserted.
Figure 36:
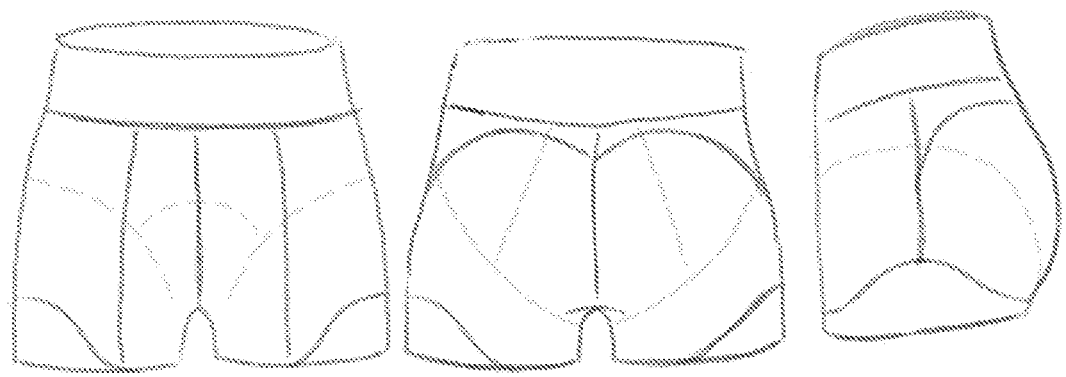
FIG. 36 shows front, rear, and side views of example short pants into which an insert for managing body fluid may be inserted.
Figure 37:
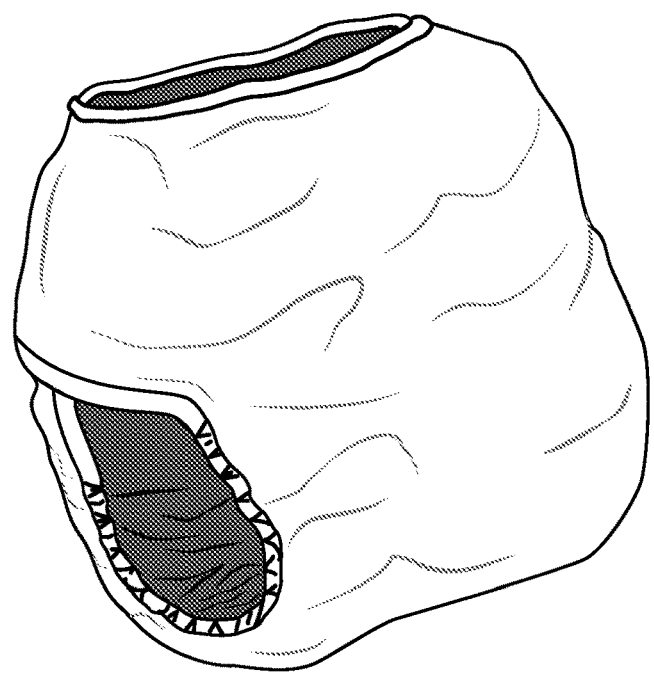
FIG. 37 shows a perspective view of an example nappy into which an insert for managing body fluid may be inserted.
Figure 38:
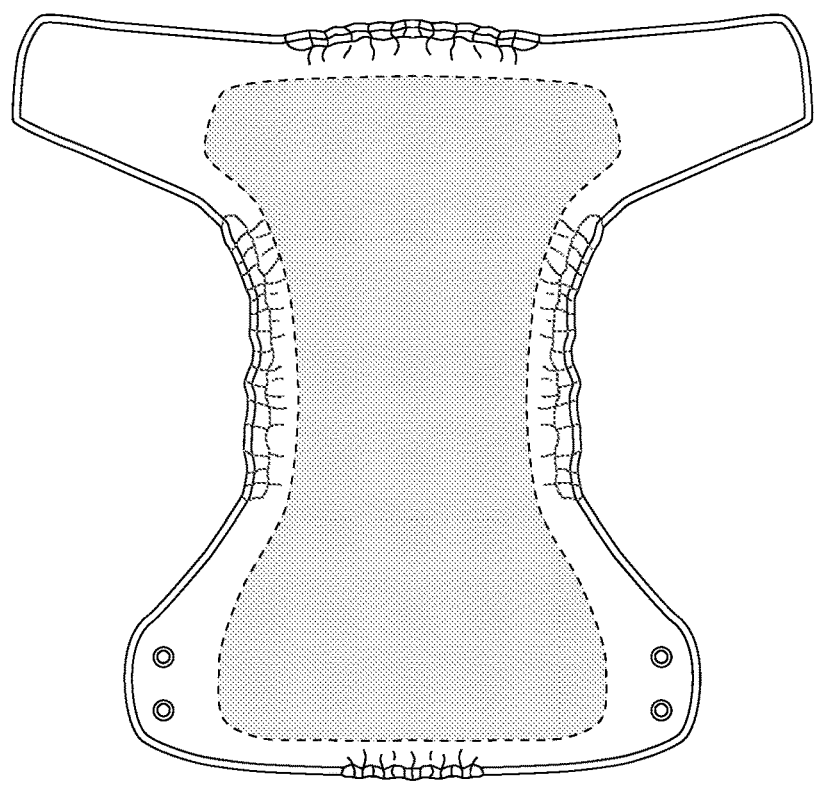
FIG. 38 shows a top view of the nappy of FIG. 37 in a splayed open arrangement.

FIG. 35 illustrates example pants, which may be long pants, trousers, yoga pants, leggings, or any other type of pants. FIG. 36 illustrates example short pants, which may be shorts, running shorts, or any other type of short pants. FIGS. 37 and 38 illustrate an example nappy or diaper. These figures show a crotch region of the pants, short pants, or nappy, located between leg openings or pant legs, into which an insert for managing body fluid discharged by a wearer of the undergarment may be inserted. The insert may comprise a middle section configured to be located between the thighs of the wearer. The insert may further comprise front and rear sections extending from the middle sections, similar to those shown in FIGS. 19 to 21, though, in some examples, larger in size or wider. The rear section of an insert for pants or short pants may extend over all or part of a back rise or seat region of the pants or short pants configured to cover the buttocks of a wearer. The front section of an insert for pants or short pants may extend over all or part of a front rise of the pants or short pants configured to cover the groin of the wearer.

It will be appreciated that the example inserts as shown in FIGS. 19 to 25 and 27 to 32, although illustrated with a particular layer configuration comprising one or two absorbent layers and one liquid barrier layer, can be varied in accordance with any layer configurations/arrangements/edge profiles as described herein, such as, for example, those described in FIGS. 1 to 17 and 39 to 42. It will thus be appreciated that FIGS. 19 to 25 and 27 to 32 are thus simply to illustrate example general shaping for the insert as whole, and to illustrate example exposed/uncovered areas of the wearer-facing side of the liquid barrier layer and example stepped edge profile positioning for the absorbent layers.

Whilst the embodiments described in detail include a combination of liquid barrier layer/s and absorbent layer/s, it will be appreciated that one inventive aspect, which is having exposed layer peripheral regions that encourage drying of discharge to form a barrier or seal, may be employed in further alternative embodiments that comprise, for example, other layer types, only absorbent layers, or only liquid barrier layers.

As outlined, the presently described inserts and/or garments including same have several features which provide improved fluid management, leakproof functionality and/or comfort for a wearer. For example, as described: the uncovered peripheral regions promote the formation of a natural seal to help stop leakage at the peripheries; the centralised stitching of absorbent layers to the initial liquid barrier layer is spaced from the edges of the insert such that any liquid seepage through the stitching is retained away from the edges of the insert; the uncovered peripheral regions provide that there is limited contact of the inner fabric layer the garment (or fluid acquisition layer) with the liquid barrier layers at the peripheral region, and, as the absorbent layers are generally inset from the edges, fluid transfer to the absorbent layers occurs centrally; the stepped/pyramidal shaped edge profile allows more absorbent layers to be included and therefore improved absorbent capacity without adding extra bulk (e.g. between the thighs) so that comfort is maintained/improved; the arrangement of the liquid barriers layers such that airflow permitted therethrough promotes drying of discharge retained between the layers; the inclusion of 2 or more liquid barrier layers and the avoidance of stitching the outermost layer assist to prevent leakage; and the configuration of the grains on the fabric of the liquid barrier layers, to encourage liquid flow to the front/back of the insert, rather than to the lateral sides, helps to direct discharge flow away from the side edge of the inset (i.e. near the leg openings). It will be appreciated that whilst each of the above features is advantageous and effective individually, all or combinations of these features also work together as a system synergistically, to provide improved performance and comfort for a wearer. The inserts and garments including same are also typically launderable (not disposable type products), such that they can be washed and re-used/worn, which reduces cost for the wearer, and is better for the environment.

Throughout this specification and the claims which follow, unless the context requires otherwise, the word "comprise", and variations such as "comprises" or "comprising", will be understood to imply the inclusion of a stated integer or step or group of integers or steps but not the exclusion ofany other integer or step or group of integers or steps.

The invention claimed is:

1. Underpants comprising a non-disposable fluid management insert secured between two fabric layers of the underpants, the insert located at a crotch region of the underpants and extending between leg openings thereof,
   wherein the insert comprises:
      a first liquid barrier layer having a wearer-facing side and an out-facing side;
      a second separate liquid barrier layer disposed adjacent to the out-facing side of the first liquid barrier layer such that an air passage is provided between the first and second liquid barrier layers; and
      a plurality of absorbent layers stacked outwardly from the wearer-facing side of the first liquid barrier layer,
   wherein the absorbent layer closest to the first liquid barrier layer covers a portion of the wearer-facing side of the first liquid barrier layer but leaves at least one peripheral region uncovered, the at least one peripheral region extending at least along the sides of the liquid barrier layer adjacent the leg openings such that the absorbent layer is spaced from the edges of the first liquid barrier layer adjacent the leg openings,
   wherein the width of each absorbent layer, as taken between sides adjacent the leg openings, decreases with each stacked absorbent layer in the direction outward from the first liquid barrier layer,
   wherein each liquid barrier layer comprises a fabric layer with a polymer film layer attached thereto, and the first and second liquid barrier layers are arranged such that the fabric layers thereof face one another, and
   wherein the first liquid barrier layer and one or more of the absorbent layers are secured together by stitching such that stitching does not extend into the second liquid barrier layer adjacent the leg openings.

2. Underpants as claimed in claim 1, wherein the insert comprises three absorbent layers.

3. Underpants as claimed in claim 1, wherein the at least one peripheral region that is left uncovered extends around the whole perimeter of the wearer-facing side of the liquid barrier layer.

4. Underpants as claimed in claim 1, wherein one or more of the absorbent layers comprise a microfibre fabric layer.

5. Underpants as claimed in claim 4, wherein the microfibre fabric comprises polyester and polyamide fibres with a linear mass density in the range from 0.45 denier to 1.20 denier.

6. Underpants as claimed in claim 1, wherein the absorbent layers comprise bamboo.

7. Underpants as claimed in claim 6, wherein the absorbent layers have a fabric weight in the range from 250 to 400 grams per square metre.

8. Underpants as claimed in claim 1, wherein the absorbent layers comprise a blend of bamboo and cotton.

9. Underpants as claimed in claim 1, wherein the insert comprises a third liquid barrier layer, the second liquid barrier layer being sandwiched between the first and third liquid barrier layers, the second liquid barrier layer having a width, as taken between sides adjacent the leg openings, that is narrower than the first and third liquid barrier layers, such that a space is provided between the first and third liquid barrier layers adjacent the leg openings, into which the second liquid barrier layer does not extend.

10. Underpants as claimed in claim 9, wherein the third liquid barrier layer comprises a fabric layer with a polymer film layer attached thereto, and the fabric layer of the third liquid barrier layer is disposed on the wearer-facing side of the third liquid barrier layer.

11. Underpants as claimed in claim 1, wherein the polymer film layer is a polyurethane layer.

12. Underpants as claimed in claim 1, wherein the fabric layer of each liquid barrier layer comprises a knitted fabric.

13. Underpants as claimed in claim 1, wherein the insert comprises a middle section located between the leg openings with concave sides that conform to the leg openings, and front and rear sections extending from the middle section.

14. Underpants as claimed in claim 1, wherein the fabric layers of the underpants between which the insert is secured are an inner fabric layer and an outer fabric layer, and wherein the liquid barrier layers of the insert are stitched to the inner fabric layer but not the outer fabric layer.

15. Underpants comprising a non-disposable fluid management insert secured between two fabric layers of the underpants, the insert located at a crotch region of the underpants and extending between leg openings thereof,
   wherein the insert comprises:
      a first liquid barrier layer having a wearer-facing side and an out-facing side;
      a second separate liquid barrier layer disposed adjacent to the out-facing side of the first liquid barrier layer such that an air passage is provided between the first and second liquid barrier layers; and
      a plurality of absorbent layers stacked outwardly from the wearer-facing side of the first liquid barrier layer,
   wherein the absorbent layer closest to the first liquid barrier layer covers a portion of the wearer-facing side of the first liquid barrier layer but leaves at least one peripheral region uncovered, the at least one peripheral region extending at least along the sides of the liquid barrier layer adjacent the leg openings such that the absorbent layer is spaced from the edges of the first liquid barrier layer adjacent the leg openings,
   wherein the width of each absorbent layer, as taken between sides adjacent the leg openings, decreases with each stacked absorbent layer in the direction outward from the first liquid barrier layer,
   wherein each liquid barrier layer comprises a fabric layer with a polymer film layer attached thereto, and the first and second liquid barrier layers are arranged such that the fabric layers thereof face one another, and
   wherein the insert comprises a third liquid barrier layer, the second liquid barrier layer being sandwiched between the first and third liquid barrier layers, the second liquid barrier layer having a width, as taken between sides adjacent the leg openings, that is narrower than the first and third liquid barrier layers, such that a space is provided between the first and third liquid barrier layers adjacent the leg openings, into which the second liquid barrier layer does not extend.

16. Underpants as claimed in claim 15, wherein the insert comprises three absorbent layers.

17. Underpants as claimed in claim 15, wherein the at least one peripheral region that is left uncovered extends around the whole perimeter of the wearer-facing side of the liquid barrier layer.

18. Underpants as claimed in claim 15, wherein the polymer film layer is a polyurethane layer.

19. Underpants as claimed in claim 15, wherein the fabric layer of each liquid barrier layer comprises a knitted fabric.

20. Underpants as claimed in claim 15, wherein the third liquid barrier layer comprises a fabric layer with a polymer film layer attached thereto, and the fabric layer of the third liquid barrier layer is disposed on the wearer-facing side of the third liquid barrier layer.

* * * * *

UNITED STATES PATENT AND TRADEMARK OFFICE
CERTIFICATE OF CORRECTION

PATENT NO. : 12,239,511 B2
APPLICATION NO. : 18/685842
DATED : March 4, 2025
INVENTOR(S) : Wesam Fawzi Ahmed It is certified that error appears in the above-identified patent and that said Letters Patent is hereby corrected as shown below:

On the Title Page

In the Applicant, item (71):
Replace applicant's name of "Wesam Fawz Ahmed" to "Wesam Fawzi Ahmed".

In the Inventor, item (72):
Replace inventor's name of "Wesam Fawz Ahmed" to "Wesam Fawzi Ahmed".

In the Assignee, item (73):
Replace assignee's name of "Wesam Fawz Ahmed" to "Wesam Fawzi Ahmed".

Signed and Sealed this
Third Day of June, 2025

Coke Morgan Stewart
*Acting Director of the United States Patent and Trademark Office*